US012226402B2

(12) United States Patent
Sasikumar et al.

(10) Patent No.: US 12,226,402 B2
(45) Date of Patent: *Feb. 18, 2025

(54) DUAL INHIBITORS OF TIM-3 AND PD-1 PATHWAYS

(71) Applicant: Aurigene Oncology Limited, Bangalore (IN)

(72) Inventors: Pottayil Govindan Nair Sasikumar, Bangalore (IN); Muralidhara Ramachandra, Bangalore (IN); Seetharamaiah Setty Sudarshan Naremaddepalli, Bangalore (IN); Nagaraj Gowda, Bangalore (IN)

(73) Assignee: Aurigene Oncology Limited, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/516,458

(22) Filed: Nov. 21, 2023

(65) Prior Publication Data

US 2024/0100024 A1 Mar. 28, 2024

Related U.S. Application Data

(63) Continuation of application No. 17/962,096, filed on Oct. 7, 2022, now abandoned, which is a continuation of application No. 16/761,162, filed as application No. PCT/IB2018/058526 on Oct. 31, 2018, now Pat. No. 11,497,734.

(30) Foreign Application Priority Data

Nov. 3, 2017 (IN) .............................. 201741039298

(51) Int. Cl.
| | | |
|---|---|---|
| *A61K 31/4245* | (2006.01) | |
| *A61K 31/454* | (2006.01) | |
| *A61K 31/5377* | (2006.01) | |
| *A61K 45/06* | (2006.01) | |

(52) U.S. Cl.
CPC ........ *A61K 31/4245* (2013.01); *A61K 31/454* (2013.01); *A61K 31/5377* (2013.01); *A61K 45/06* (2013.01)

(58) Field of Classification Search
CPC .............. C07D 271/06; A61K 31/4245; A61K 31/5377
See application file for complete search history.

(56) References Cited

U.S. PATENT DOCUMENTS

| | | | |
|---|---|---|---|
| 3,227,725 A | 1/1966 | Fernand et al. | |
| 5,387,585 A | 2/1995 | Borer et al. | |
| 5,665,718 A | 9/1997 | Godel et al. | |
| 8,735,553 B1 | 5/2014 | Li et al. | |
| 9,771,338 B2 | 9/2017 | Sasikumar et al. | |
| 10,173,989 B2 | 1/2019 | Sasikumar et al. | |
| 10,590,093 B2 | 3/2020 | Sasikumar et al. | |
| 10,781,189 B2 | 9/2020 | Sasikumar et al. | |
| 10,961,205 B2 | 3/2021 | Sasikumar et al. | |
| 11,040,948 B2 | 6/2021 | Yu | |
| 11,136,300 B2 | 10/2021 | Sasikumar et al. | |
| 11,465,976 B2 | 10/2022 | Sasikumar et al. | |
| 11,497,734 B2 | 11/2022 | Sasikumar et al. | |
| 11,497,735 B2 | 11/2022 | Sasikumar et al. | |
| 11,939,306 B2 | 3/2024 | Yu | |
| 12,064,418 B2 | 8/2024 | Sasikumar et al. | |
| 2005/0272779 A1 | 12/2005 | Edwards et al. | |
| 2007/0197522 A1 | 8/2007 | Edwards et al. | |
| 2007/0225332 A1 | 9/2007 | Gu et al. | |
| 2009/0099227 A1 | 4/2009 | Fyfe et al. | |
| 2011/0275673 A1 | 11/2011 | Xiang et al. | |
| 2013/0022629 A1 | 1/2013 | Sharpe et al. | |
| 2014/0199334 A1 | 7/2014 | Sasikumar et al. | |
| 2014/0235620 A1 | 8/2014 | Caferro et al. | |
| 2015/0073024 A1 | 3/2015 | Sasikumar et al. | |
| 2015/0073042 A1 | 3/2015 | Sasikumar et al. | |
| 2018/0044303 A1 | 2/2018 | Sasikumar et al. | |
| 2020/0061030 A1 | 2/2020 | Sasikumar et al. | |
| 2020/0239422 A1 | 7/2020 | Sasikumar et al. | |
| 2020/0247766 A1 | 8/2020 | Yu | |
| 2020/0289477 A1 | 9/2020 | Sasikumar et al. | |
| 2020/0368210 A1 | 11/2020 | Sasikumar et al. | |
| 2021/0380544 A1 | 12/2021 | Yu | |
| 2022/0048875 A1 | 2/2022 | Sasikumar et al. | |

(Continued)

FOREIGN PATENT DOCUMENTS

| | | |
|---|---|---|
| JP | 2016-532710 A | 10/2016 |
| JP | 2016-539662 A | 12/2016 |
| KR | 2016/0081897 A | 7/2016 |

(Continued)

OTHER PUBLICATIONS

Alsaab et al., "PD-1 and PD-L1 Checkpoint Signaling Inhibition for CancerImmunotherapy: Mechanism, Combinations, and Clinical Outcome" Frontiers in Pharmacology, vol. 8, No. 561 (2017).

Anderson et al., "Lag-3, Tim-3, and TIGIT: Co-inhibitory Receptors with Specialized Functions in Immune Regulation," Immunity, 44(5): 989-1004 (2016).

Ansell, "PD-1 Is Expressed on B-Cells in Waldenstrom Macroglobulinemia and Promotes Malignant Cell Viability and Proliferation" Blood, vol. 124, No. 21 (2014).

Ardestani et al., "Cell death features induced in Leishmania major by 1,3,4-thiadiazole derivatives," Exp Parasitol, 132(2): 116-122 (2012).

(Continued)

*Primary Examiner* — Kamal A Saeed

(74) *Attorney, Agent, or Firm* — Foley Hoag LLP; David P. Halstead; Alexander J. Chatterley

(57) ABSTRACT

The present disclosure relates to 3-substituted 1,2,4-oxadiazole compounds and their derivatives, which are useful as T-cell immunoglobulin and mucin-domain containing-3 (TIM-3) inhibitors or as dual inhibitors of TIM-3 and the programmed cell death 1 (PD-1) signaling pathway. The disclosure also relates to treatment of disorders by inhibiting an immunosuppressive signal induced by TIM-3, PD-1, PD-L1, and/or PD-L2.

14 Claims, No Drawings

(56) References Cited

U.S. PATENT DOCUMENTS

2024/0182433 A1  6/2024  Yu

FOREIGN PATENT DOCUMENTS

| | | |
|---|---|---|
| WO | WO-2001/14557 A1 | 3/2001 |
| WO | WO-2002/079499 A1 | 10/2002 |
| WO | WO-2002/086083 A2 | 10/2002 |
| WO | WO-2003/042402 A2 | 5/2003 |
| WO | WO-2003/070711 A1 | 8/2003 |
| WO | WO-2004/004771 A1 | 1/2004 |
| WO | WO-2004/056875 A1 | 7/2004 |
| WO | WO-2005/056550 A2 | 6/2005 |
| WO | WO-2006/121168 A1 | 11/2006 |
| WO | WO-2006/133216 A2 | 12/2006 |
| WO | WO-2007/075749 A2 | 7/2007 |
| WO | WO-2008/011557 A2 | 1/2008 |
| WO | WO-2008/039431 A2 | 4/2008 |
| WO | WO-2008/156712 A1 | 12/2008 |
| WO | WO-2009/006555 A2 | 1/2009 |
| WO | WO-2009/059162 A1 | 5/2009 |
| WO | WO-2009/105712 A1 | 8/2009 |
| WO | WO-2010/051447 A1 | 5/2010 |
| WO | WO-2010/077634 A1 | 7/2010 |
| WO | WO-2011/066389 A1 | 6/2011 |
| WO | WO-2011/082400 A2 | 7/2011 |
| WO | WO-2011/137587 A1 | 11/2011 |
| WO | WO-2011/161699 A2 | 12/2011 |
| WO | WO-2012/129564 A2 | 9/2012 |
| WO | WO-2012/168944 A1 | 12/2012 |
| WO | WO-2013/132317 A1 | 9/2013 |
| WO | WO-2013/144704 A1 | 10/2013 |
| WO | WO-2014/055897 A2 | 4/2014 |
| WO | WO-2014/059173 A2 | 4/2014 |
| WO | WO-2014/100079 A1 | 6/2014 |
| WO | WO-2014/110298 A1 | 7/2014 |
| WO | WO-2014/141104 A1 | 9/2014 |
| WO | WO-2014/147586 A1 | 9/2014 |
| WO | WO-2015/033299 A1 | 3/2015 |
| WO | WO-2015/033301 A1 | 3/2015 |
| WO | WO-2016/073470 A1 | 5/2016 |
| WO | WO-2016/142833 A1 | 9/2016 |
| WO | WO-2016/142852 A1 | 9/2016 |
| WO | WO-2016/142886 A2 | 9/2016 |
| WO | WO-2018/047143 A1 | 3/2018 |
| WO | WO-2018/073754 A1 | 4/2018 |
| WO | WO-2019/061324 A1 | 4/2019 |
| WO | WO-2019/067678 A1 | 4/2019 |
| WO | WO-2019/087087 A1 | 5/2019 |

OTHER PUBLICATIONS

Berge et al., "Pharmaceutical Salts," Journal of Pharmaceutical Sciences, 66(1):1-19 (1977).
Booher et al., "Combination of IRAK4 Inhibitor CA-4948 with BCL2 Inhibitor Venetoclax Induces Tumor Regression in an ABC-DLBCL Xenograft Model", Blood, 130(1): 1534, (2017).
Borg et al., "1,2,4-Oxadiazole Derivatives of Phenylalnine: Potential Inhibitors of Substance P Endopeptidase," Eur. J. Med. Chem., 28(10):801-810 (1993).
Brittain. "Polymorphism in pharmaceutical solids," edited by H.G Brittain, D.J.W. Grant (chapter 1) p. 1-10 and J.K. Guillory (Chapter 5) p. 183-226 (1999).
Byrn et al., "Pharmaceutical Solids: A Strategic Approach to Regulatory Considerations," Pharmaceutical Research, 12(7):945-954 (1995).
CAS Registry No. 1252104-30-5 (2013).
CAS Registry No. 1356744-17-6 (2012).
CAS Registry No. 146429-76-5 (2013).
CAS Registry No. 1494629-78-5 (2013).
CAS Registry No. 1496514-97-6 (2013).
CAS Registry No. 1496518-51-4 (2013).
CAS Registry No. 1557852-63-7 (2014).
CAS Registry No. 1848907-06-1 (2016).
CAS Registry No. 1848909-97-6 (2016).
CAS Registry No. 1857027-85-0 (2016).
CAS Registry No. 1868314-35-5 (2016).
CAS Registry No. 1868388-36-6 (2016).
CAS Registry No. 1868393-26-3 (2016).
CAS Registry No. 1869758-25-7 (2016).
CAS Registry No. 1870159-31-1 (2016).
CAS Registry No. 1875311-16-2 (2016).
CAS Registry No. 1875758-09-0 (2016).
CAS Registry No. 1878569-90-4 (2016).
CAS Registry No. 876710-85-9 (2006).
Cedres et al., "Analysis of Expression of Programmed Cell Death 1 Ligand 1 (PD-L1) in Malignant Pleural Mesothelioma (MPM)" Plos One DOI:10.1371 (2015).
Censi et al., "Polymorph Impact on the Bioavailability and Stability of Poorly Soluble Drugs," Molecules, 20(10): 18759-18776 (2015).
Clinical Trial NCT 02812875., "A Study of CA-170 (Oral PD-L1, PD-L2 and VISTA Checkpoint Antagonist) in Patients With Advanced Tumors and Lymphomas," U.S. National Library of Medicine: 7 pages (2016).
Clinical Trial NCT02671955., "A Study of Safety, Pharmacokinetics, Pharmacodynamics of JNJ-61610588 in Participants With Advanced Cancer," U.S. National Library of Medicine: 9 pages (2016).
Curiel et al., "Blockade of B7-H1 improves myeloid dendritic cell-mediated anitumor immunity" Nature Medicine, vol. 9, No. 5 (2003).
Database Registry Chemical Abstracts, STN Accession No. 172410-37-6.
Database Registry Chemical Abstracts, STN Accession No. 197083-27-5.
Dempke et al., "Second-and third-generation drugs for immuno-oncology treatment—The more the better?" Eur J Cancer, 74: 55-72 (2017).
Deng et al., "A New VISTA on combination therapy for negative checkpoint regulator blockade" Journal for Immunotherapy of Cancer, 4(86): 1-7 (2016).
Extended European Search Report for EP Application No. 16761169.8 mailed Jul. 2, 2019.
Extended European Search Report for EP Application No. 16761184 mailed Jun. 26, 2018.
Extended European Search Report for EP Application No. 17862427.6 dated Jun. 5, 2020.
Extended European Search Report for EP Application No. 21209727.3 dated May 18, 2022.
Extended European Search Report for EP Application No. EP/US18/18863750 mailed May 31, 2021.
Extended European Search Report for European Application No. 18162983.3 dated Jun. 27, 2018.
Graham, "Clinical Trials of HIV Vaccines," HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM, pp. 1-20-38.
Guo et al., "Design of oxobenzimidazoles and oxindoles as novel androgen receptor antagonists," Bioorg Med Chem Letts 22(7):2572-2578 (2012).
Harvey, "Immunologic and Clinical Effects of Targeting PD-1 in Lung Cancer," Nature, 96: 214-223 (2014).
Hirayama "Handbook for preparation of crystal of organic compound", Maruzen Co., Ltd 17-23, 37-40, 45-51, 57-65 (2008).
International Preliminary Report on Patentability for International Application No. PCT/IB2018/058526 mailed May 14, 2020.
International Search Report and Written Opinion for International Application No. PCT/CN2017/104485 dated Jun. 29, 2018.
International Search Report and Written Opinion for International Application No. PCT/IB2014/064279 mailed Dec. 12, 2014.
International Search Report and Written Opinion for International Application No. PCT/IB2016/051266 mailed Jul. 8, 2016.
International Search Report and Written Opinion for International Application No. PCT/IB2016/051343 mailed Jul. 28, 2016.
International Search Report and Written Opinion for International Application No. PCT/IB2017/056462 dated Jan. 10, 2018.

(56) References Cited

OTHER PUBLICATIONS

International Search Report Written Opinion for International Application No. PCT/US2018/053052 dated Jan. 29, 2019.
Jin, "Role of PD-1 in Regulating T-Cell Immunity," Current Topics in Microbiology and Immunology, 350: 17-37 (2010).
Lazorchak et al., "Abstract A36: CA-170, an oral small molecule PD-L1 and VISTA immune checkpoint antagonist, promotes T cell immune activation and inhibits tumor growth in pre-clinical models of cancer," Cancer Immunology Research, 5(S3):A36 (2017).
Lee, "A practical guide to pharmaceutical polymorph screening & selection," Asian J Pharm Sci, 9(4): 163-175 (2014).
Liu et al., "Immune-checkpoint proteins VISTA and PD-1 nonredundantly regulate murine T- cell responses," PNAS, 112(21): 6682-6687 (2015).
Luo et al., "Principles of Cancer Therapy: Oncogene and Non-oncogene Addiction," Cell, 136(5): 823-837 (2009).
Marechal et al., "1,2,4-oxadiazoles identified by virtual screening and their non-covalent inhibition of the human 20S proteasome," Curr Med Chem 20(18):2351-2362 (2013).
Melero, "Evolving Synergistic Combinations of Targeted Immunotherapies to Combat Cancer", Nature Reviews Cancer 15:457-472 (2015).
Moussebois et al., "Synthese de Deux Nouveaux Acides Amines Phenoliques Comportant un Cycle 1,2,4-Oxadiazole," Helv. Chim. ACTA, 60(1):237-242 (1977).
Newman, "Specialized Solid Form Screening Techniques," Org Process Res Dev, 13(3): 457-471 (2012).
Ozcan et al., "Oxadiazole-Isopropylamieds as Potent and Noncovalent Proteasome Inhibitors," J. Med. Chem., 56(10):3783-3805 (2013).
Palazzo et al., "1,2,4-Oxadiazoles—IV. Synthesis and Pharmacological Properties of a Series of Substituted Aminoalkyl- 1,2,4-Oxadiazoles," J. Med. Chem., 351-367 (1961).
Patwardhan et al., "Structure-Activity Relationship Studies and in Vivo Activity of Guanidine-Based Sphingosine Kinase Inhibitors: Discovery of SphK1- and SphK2—Selective Inhibitors," J. Med. Chem., 58(4):1879-1899 (2015).
Pedoeem et al., "Programmed Death-1 Pathway in Cancer and Autoimmunity," Clinical Immunology, 153: 145-152 (2014).
Rabadi et al., ""The role of VISTA in the tumor microenvironment"" Journal of Cancer Metastasis and Treatment, 8(24): 1-14 (2022).
Rietz et al., "Fragment-Based Discovery of Small Molecules Bound to T-Cell Immunoglobulin and Mucin Domain-Containing Molecule 3 (TIM-3)," J Med Chem, 64: 14757-14772 (2021).
Sasikumar et al., "PD-1 derived CA-170 is an oral immune checkpoint inhibitor that exhibits preclinical anti-tumor efficacy," Communications Biology, 4: 12 pages (2021).
Shi et al., "The Role of PD-1 and PD-L1 in T-cell Immune Suppression in Patients with Hematological Malignancies," Journal of Hematology & Oncology, 6(74): 1-6 (2013).
Skrdla et al., "A Simple Quantitative FT-IR Approach for the Study of a Polymorphic Transformation Under Crystallization Slurry Conditions", Journal of Pharmaceutical and Biomedical Analysis, 25(5-6): 731-739 (2001).
Sureshbabu et al., "Synthesis of 1,2,4-oxadiazole-linked Orthogonally Urethane-Protected Dipeptide Mimetics," Tetrahedron Letters, 49(35): 5133-5136 (2008).
Swaika et al., "Current state of anti-PD-L1 and anti-PD-1 agents in cancer therapy" Molecular Immunology (2015).
Tagliamento et al., "VISTA: A Promising Target for Cancer Immunotherapy?" ImmunoTargets and Therapy, 10: 185-200 (2021).
Takada, "API form screening and selection in drug discovery stage", Pharm Stage, 6(10):20-25. (2007).
Waldmann, "Effective Cancer Therapy Through Immunomodulation," T Annu Rev Med, 57: 65-81 (2006).
Wu et al., "VISTA inhibitors in cancer immunotherapy: a short perspective on recent progresses," RSC Med Chem, 12: 1672-1679 (2021).
U.S. Appl. No. 15/556,800, Granted.
U.S. Appl. No. 16/945,854, Granted.
U.S. Appl. No. 17/962,976, Pending.
U.S. Appl. No. 15/298,539, Granted.
U.S. Appl. No. 15/713,671, Granted.
U.S. Appl. No. 16/192,030, Granted.
U.S. Appl. No. 16/806,872, Granted.
U.S. Appl. No. 17/192,279, Granted.
U.S. Appl. No. 17/981,695, Pending.
U.S. Appl. No. 16/343,681, Pending.
U.S. Appl. No. 16/761,162, Granted.
U.S. Appl. No. 17/962,096, Allowed.
U.S. Appl. No. 16/651,830, Granted.
U.S. Appl. No. 17/350,445, Granted.
U.S. Appl. No. 18/101,387, Allowed.
U.S. Appl. No. 16/755,439, Granted.
U.S. Appl. No. 17/461,512, Granted.
U.S. Appl. No. 18/197,414, Pending.
U.S. Appl. No. 16/761,964, Granted.
U.S. Appl. No. 17/960,586, Pending.
Lazorchak et al., "An oral small molecule combination therapy targeting PD-L1, VISTA and Tim-3 immune inhibitory checkpoints exhibits enhanced anti-tumor efficacy in pre-clinical models of cancer," Journal for Immunotherapy of Cancer 5.2 (2017): p. 279, p. 28.
Lazorchak et al., "An oral small molecule combination therapy targeting PD-L1, VISTA and Tim-3 immune inhibitory checkpoints exhibits enhanced anti-tumor efficacy in pre-clinical models of cancer," Published by Curis, Nov. 8, 2017.
LeMercier et al., "VISTA regulates the development of protective antitumor immunity." Cancer Research 74(7) (2014): 1933-1944.
Sasikumar et al., "Oral immune checkpoint antagonists targeting PD-L1/VISTA and PD-L1/Tim3 for cancer therapy," Cancer Research 76.14 (Jul. 31, 2016).
Sasikumar et al., "Oral immune checkpoint antagonists targeting PD-L1/VISTA and PD-L1/Tim3 for cancer therapy," Published by Curis, Oct. 1, 2019.

DUAL INHIBITORS OF TIM-3 AND PD-1 PATHWAYS

CROSS-REFERENCE TO RELATED APPLICATION

This application is a continuation of U.S. application Ser. No.: 17/962096, filed Oct. 7, 2022, which is a continuation of U.S. application Ser. No.: 16/761,162, filed May 1, 2020, now U.S. Pat. No. 11,497,734, which is the § 371 National Stage of PCT/IB2018/058526, filed Oct. 31, 2018, which claims the benefit of Indian provisional application No. 20/174,1039298, filed on Nov. 3, 2017; the contents of each of which are hereby incorporated by reference in their entirety.

TECHNICAL FIELD

The disclosure relates to pharmaceutical compositions comprising 3-substituted 1,2,4-oxadiazole compounds and their derivatives, which are useful as TIM-3 inhibitors or as dual inhibitors of TIM-3 and PD-1 (e.g., PD-1. PD-L1. or PD-L2) pathways.

BACKGROUND

Immune system in mammals sustains the ability to control the homeostasis between the activation and inactivation of lymphocytes through various regulatory mechanisms during and after an immune response. Among these mechanisms, there are mechanisms that specifically modulate the immune response as and when required.

T-cell immunoglobulin and mucin-domain containing-3 (TIM-3 or Hepatitis A

Virus Cellular Receptor 2 (HAVCR2)) is an immune checkpoint regulator that directly limits the duration and magnitude of IFN-γ-producing CD4$^+$ T helper 1 (Th1) and CD8$^+$ T cytotoxic 1 (Tc1) T cell responses. TIM-3 protein is a type I transmembrane protein with an immunoglobulin variable (IgV) domain and a mucin domain. TIM-3 is expressed on T cells and on phagocytic cells such as macrophages and dendritic cells.

TIM-3 can bind a protein ligand (e.g., S-type lectin galectin-9, Gal-9, CEACAM1, and LILRA3) and can inhibit the Th1 response by inducing apoptosis. TIM-3 is expressed on dysfunctional CD8$^+$ T cells and Tregs, which lead to immunosuppression in tumor tissue.

PD-1 (or Program Death Domain-1 or Programmed Cell Death 1 or PDCD1) is a ~55 kDa type I membrane glycoprotein and is a receptor of the CD28 superfamily that negatively regulates T cell antigen receptor signaling by interacting with the specific ligands and is suggested to play significant role in the maintenance of self-tolerance. The PD-1 protein's structure comprises an extracellular IgV domain followed by a trans-membrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals. Also, PD-1 is expressed on the surface of activated T cells, B cells, and macrophages. (Y. Agata et al., Int. Immunol. 1996, 8: 765) suggesting that compared to CTLA-4 [(Cytotoxic T-Lymphocyte Antigen 4), also known as CD152 (Cluster of differentiation 152), a protein that also plays an important regulatory role in the immune system], PD-1 more broadly negatively regulates immune responses.

Blockade of PD-1, an inhibitory receptor expressed by T cells, can overcome immune resistance. PD-1 is a key immune check point receptor expressed by activated T cells, and it mediates immune suppression. PD-1 functions primarily in peripheral tissues, where T cells may encounter the immune suppressive PD-1 ligands; PD-L1 (B7-H1) and PD-L2 (B7-DC), which are expressed by tumor cells, stromal cells, or both. Inhibition of the interaction between PD-1 and PD-L1 can enhance T-cell responses in vitro and mediate preclinical antitumor activity (S. L. Topalian et al., N. Engl. J. Med. 2012, 366(26): 2443-2454).

PD-1 functions as an immune checkpoint protein that suppresses T-cell activation. TIM-3 is an immune checkpoint receptor that limits the duration and magnitude of Th1 and Tc1 T-cell responses. Ligand binding by the TIM-3 receptor triggers downstream signaling to negatively regulate T-cell survival and function. Blockade of TIM-3 and the PD-1/PD-L1 pathways likely nonredundantly regulate T-cell responses. TIM-3 and PD-1 relate to almost every aspect of immune responses including autoimmunity, tumor immunity, infectious immunity, transplantation immunity, and immunological privilege. PD-1 plays critical roles in the regulation of the immune response to cancer, allergy, and chronic viral infection (J. R. Brahmer et al., N. Engl. J. Med. 2012, 366(26): 2455-2465).

Indeed, functional "exhaustion" (immune dysfunction) among T and B cell subsets is a well-described feature of chronic viral infections, such as hepatitis B and C and HIV viruses. T cell exhaustion was initially described for CD8 T cells in mice chronically infected with lymphocytic choriomeningitis virus clone 13. In the lymphocytic choriomeningitis virus mouse model, repeated antigen stimulation through the T cell antigen receptor drives the sustained expression of T cell inhibitory receptors, including programmed cell death-1 (PD-1) and lymphocyte activation gene-3 (LAG-3). on virus-specific CD8 T cells (J. Illingworth et al., J. Immunol. 2013, 190(3): 1038-1047). Tumor cells and virus (including HCV and HIV) infected cells are known to exploit the PD-1 signaling pathway (to create immunosuppression) in order to escape immune surveillance by host T cells. TIM-3 is selectively expressed on T cells, and seems to be expressed primarily in intratumor cells (A. C. Anderson, Cancer Immunol. Res., 2014, 2(5): 393-398). Blockade of PD-1 and TIM-3 can reverse T cell exhaustion and restore anti-tumor immunity and the combined blockade of PD-1 and TIM-3 pathways was more effective in controlling tumor growth than blocking either checkpoint alone (Sakuishi et al. J. Exp. Med. 2010, 207, 2187-2194).

International applications WO2011161699 and WO2012168944 report peptides and their derivatives derived from PD-1 ectodomain capable of inhibiting the programmed cell death 1 (PD-1) signaling pathway. Further, WO2013144704 and WO2013132317 report cyclic peptides and peptidomimetic compounds as therapeutic agents capable of inhibiting the PD-1 protein, respectively. WO2015033299 and WO2016142833 report 1,2,4-oxadiazole compounds as therapeutic agents capable of inhibiting the PD-1 protein, respectively.

For the above stated reasons, there is also a need for immune modulators of TIM-3. There is also a need for more potent, additive or synergistic immune modulators of the TIM-3 and the PD-1 (e.g., PD-1, PD-L1, or PD-L2) pathways.

SUMMARY

The present disclosure relates to a method of modulating TIM-3 with a 3-substituted 1,2,4-oxadiazole compound, or a pharmaceutically acceptable salt thereof. In certain embodiments, the disclosure relates to a method of modulating the TIM-3 and the PD-1 (e.g., PD-1, PD-L1, or PD-L2) pathways with a 3-substituted 1,2,4-oxadiazole compound, or a pharmaceutically acceptable salt thereof.

In one aspect, the present disclosure provides a method of modulating an immune response mediated by T-cell immunoglobulin and mucin-domain containing-3 (TIM-3) activity in a cell, comprising contacting the cell with a compound of Formula (I), or a pharmaceutically acceptable salt thereof:

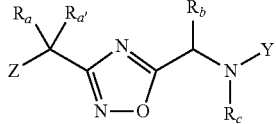

Formula (I)

wherein:
Z represents —OH or —NH-G;
G represents hydrogen or $(C_1-C_6)$alkyl;
Y represents hydrogen or a group represented by the following structural formula

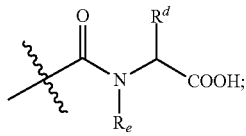

$R_a$ represents $(C_1-C_6)$alkyl substituted with —OH, —$NR_xR_y$, —$SR_x$, carboxylic acid, guanidino, or aryl, wherein the aryl group is optionally further substituted with hydroxyl; or $R_a$ and G taken together with the atom to which they are attached form a 5- to 6-membered ring containing 1 to 3 heteroatoms selected from O, N or S;
$R_{a'}$ represents hydrogen; or $R_a$ and $R_{a'}$ taken together with the atom to which they are attached form a 5- to 6-membered ring, optionally containing 1 to 3 heteroatoms selected from O, N or S;
$R_b$ represents $(C_1-C_6)$alkyl, optionally substituted with —$C(O)NR_xR_y$, —$NR_xR_y$, or carboxylic acid;
$R_c$ represents hydrogen; or $R_b$ and $R_c$ taken together with the atoms to which they are attached form a 5- to 6-membered ring containing 1 to 3 heteroatoms selected from O, N or S, wherein the 5- to 6-membered ring is optionally further substituted with hydroxyl;
$R_d$ represents $(C_1-C_6)$alkyl, optionally substituted with —$OR_x$, carboxylic acid, or aryl-OH;
$R_e$ represents hydrogen; or $R_d$ and $R_e$ taken together with the atoms to which they are attached form a 5- to 6-membered ring containing 1 to 3 heteroatoms selected from O, N or S; and
$R_x$ and $R_y$ independently represent hydrogen. $(C_1-C_6)$alkyl or $(C_2-C_6)$acyl.

In some embodiments of the methods disclosed herein, the immune response is further mediated by the programmed cell death 1 (PD-1) signaling pathway (e.g., PD-1, PD-L1, or PD-L2).

In some embodiments of the methods disclosed herein, the immune response is further mediated by a TIM-3 agent.

In another aspect, the present disclosure relates to a pharmaceutical composition comprising a compound of Formula (I), or a pharmaceutically acceptable salt and processes for preparing such compositions.

In yet another aspect, the present disclosure provides use of 3-substituted 1,2,4-oxadiazole compounds and derivatives of formula (I), or pharmaceutically acceptable salts thereof, which are capable of suppressing and/or inhibiting T-cell immunoglobulin and mucin-domain containing-3 (TIM-3) activity. In certain embodiments, the present disclosure provides use of 3-substituted 1,2,4-oxadiazole compounds and derivatives of formula (I), or pharmaceutically acceptable salts thereof, which are capable of suppressing and/or inhibiting TIM-3 and the programmed cell death 1 (PD-1) (e.g., PD-1, PD-L1, or PD-L2) signaling pathways. For example, these compounds can be used to treat one or more diseases characterized by aberrant or undesired activity of TIM-3 or by aberrant or undesired activity of the TIM-3 and the PD-1 (e.g., PD-1, PD-L1, or PD-L2) pathways.

DETAILED DESCRIPTION

The present disclosure provides 3-substituted 1,2,4-oxadiazole compounds and their derivatives as therapeutic agents useful for treatment of disorders via immunopotentiation comprising inhibition of immunosuppressive signal induced due to TIM-3 and therapies using them. In certain embodiments, the disclosure provides 3-substituted 1,2,4-oxadiazole compounds and their derivatives as therapeutic agents useful for treatment of disorders via immunopotentiation comprising inhibition of immunosuppressive signal induced due to PD-1, PD-L1, PD-L2, and/or TIM-3 and therapies using them.

Each embodiment is provided by way of explanation of the disclosure, and not by way of limitation of the disclosure. In fact, it will be apparent to those skilled in the art that various modification and variations can be made in the present disclosure without departing from the scope or spirit of the disclosure. For instance, features illustrated or described as part of one embodiment can be used on another embodiment to yield a still further embodiment. Thus it is intended that the present disclosure cover such modifications and variations as come within the scope of the appended claims and their equivalents. Other objects, features, and aspects of the present disclosure arc disclosed in, or can be derived from, the following detailed description. It is to be understood by one of ordinary skill in the art that the present discussion is a description of exemplary embodiments only, and is not to be construed as limiting the broader aspects of the present disclosure.

Methods of Treatment

T-cell immunoglobulin and mucin-domain containing-3 (TIM-3) functions as an immune checkpoint receptor that limits T-cell survival and function. TIM-3 is expressed on certain T cells. Programmed cell death protein 1 (PD-1) functions as an immune checkpoint protein that suppresses T-cell activation. TIM-3 and the PD-1/PD-L1 pathways likely nonredundantly regulate T-cell responses. TIM-3 and the PD-1 (e.g., PD-1, PD-L1, or PD-L2) pathways have been implicated in a number of diseases and conditions, and TIM-3 and the PD-1 (e.g., PD-1, PD-L1, or PD-L2) pathways are known to regulate various immune responses. Numerous studies have sought to activate immune response by targeting TIM-3 pathway or the PD-1 (e.g., PD-1, PD-L1, or PD-L2) pathway, thereby providing a therapy for certain conditions, such as cancers and autoimmune disorders. For example, combinatorial treatment using TIM-3-Fc fusion protein or gal-9 knock out mice combined with PD-L1- specific monoclonal antibodies achieved synergistic therapeutic efficacy in an acute myelogenous leukemia model showing tumor regression and improved survival (Q. Zhou et al., Blood, 2011, 117: 4501-4510). PD-1 activity has also been associated with autoimmune conditions, such as lupus erythematosus, juvenile idiopathic arthritis, and allergic encephalomyelitis. In addition, blockade of the PD-1 pathway and inhibition of TIM-3 restores function to dysfunctional $CD8^+$ T cells (e.g., restoring tumor antigen-specific IFN-γ production) and deprograms potent intratumoral Tregs (e.g., drives the downmodulation of several genes associated with potent Treg-suppressor function) (A. C. Anderson, Cancer Immunol. Res., 2014, 2(5): 393-398).

In some embodiments, the disclosure provides uses of a compound of Formula (I) of the present disclosure in inhibiting TIM-3.

In certain embodiments, the disclosure provides uses of a compound of Formula (I) in modulating an immune response mediated by TIM-3 activity and the PD-1 pathway (e.g., PD-1, PD-L1, or PD-L2) in a cell.

In certain embodiments, the present disclosure provides a method of modulating an immune response mediated by TIM-3 activity in a cell, comprising contacting the cell with a compound of Formula (I), or a pharmaceutically acceptable salt thereof:

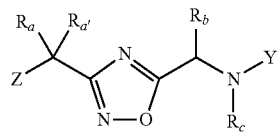

Formula (I)

wherein:
$Z$ represents —OH or —NH-G;
$G$ represents hydrogen or $(C_1-C_6)$alkyl;
$Y$ represents hydrogen or a group represented by formula

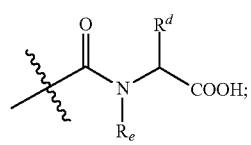

$R_a$ represents $(C_1-C_6)$alkyl substituted with —OH, —$NR_xR_y$, —$SR_x$, carboxylic acid, guanidino, or aryl, wherein the aryl group is optionally further substituted with hydroxyl; or $R_a$ and $G$ taken together with the atom to which they are attached form a 5- to 6-membered ring containing 1 to 3 heteroatoms selected from O, N or S;

$R_{a'}$ represents hydrogen; or $R_a$ and $R_{a'}$ taken together with the atom to which they are attached form a 5- to 6-membered ring, optionally containing 1 to 3 heteroatoms selected from O, N or S;

$R_b$ represents $(C_1-C_6)$alkyl, optionally substituted with —C(O)$NR_xR_y$, —$NR_xR_y$, or carboxylic acid;

$R_c$ represents hydrogen; or $R_b$ and $R_c$ taken together with the atoms to which they are attached form a 5- to 6-membered ring containing 1 to 3 heteroatoms selected from O, N or S, wherein the 5- to 6-membered ring is optionally further substituted with hydroxyl;

$R_d$ represents $(C_1-C_6)$alkyl, optionally substituted with —$OR_x$, carboxylic acid, or aryl-OH;

$R_e$ represents hydrogen; or $R_d$ and $R_e$ taken together with the atoms to which they are attached form a 5- to 6-membered ring containing 1 to 3 heteroatoms selected from O, N or S; and $R_x$ and $R_y$ independently represent hydrogen, $(C_1-C_6)$alkyl or $(C_2-C_6)$acyl.

In some embodiments of Formula (I), Z represents —NH-G. In some embodiments, G represents hydrogen or methyl. In some embodiments. G represents hydrogen.

Alternatively, in some embodiments of Formula (I), Z represents —OH.

In some embodiments, $R_a$ represents $(C_1-C_4)$alkyl, wherein $(C_1-C_4)$alkyl is substituted with —OH, —$NR_xR_y$, —NH—C(=NH)—$NH_2$, —$SR_x$, carboxylic acid, or aryl, wherein the aryl group is optionally further substituted with hydroxyl. In certain embodiments of Formula (I), $R_a$ represents $(C_1-C_4)$alkyl substituted with —OH, —$NH_2$, —NH—C(=NH)—$NH_2$, —$SCH_3$, carboxylic acid, phenyl, or p-OH (phenyl); and $R_{a'}$ is hydrogen. In certain embodiments of Formula (I), $R_a$ represents $(C_1-C_4)$alkyl substituted with —OH, —$NH_2$, —NH—C(=NH)—$NH_2$, carboxylic acid, or phenyl; and $R_{a'}$ is hydrogen. In some embodiments, $R_a$ represents —$CH_2OH$, —$CH(CH_3)OH$, —$(CH_2)_4$—$NH_2$, —$(CH_2)_2$—$SCH_3$, —$(CH_2)_2C(O)OH$, —$(CH_2)_3$—NH—C(=NH)—$NH_2$, —$CH_2$-(phenyl), or —$CH_2$-(p-OH(phenyl)). In some embodiments. $R_a$ represents —$CH_2OH$, —$CH(CH_3)OH$, —$(CH_2)_4$—$NH_2$, —$(CH2)_2C(O)OH$, —$(CH_2)_3$—NH—C(=NH)—$NH_2$, or —$CH_2$-(phenyl). In certain embodiments. $R_a$ represents —$CH_2OH$ or —CH($CH_3$)OH. In some embodiments, $R_a$ represents —$CH_2OH$.

Alternatively, in some embodiments, $R_a$ and G taken together with the atoms to which they are attached form a 5- to 6-membered ring containing 1 to 3 heteroatoms selected from O, N or S. In some embodiments, the 5- to 6-membered ring is a morpholine ring.

Alternatively, in certain embodiments, $R_a$ and $R_{a'}$ taken together with the atoms to which they are attached form a 5- to 6-membered ring, optionally containing 1 to 3 heteroatoms selected from O, N or S. In some embodiments, the 5- to 6-membered ring is a cyclopentyl ring.

In certain embodiments, $R_b$ represents $(C_1-C_4)$alkyl, wherein $(C_1-C_4)$alkyl is optionally substituted with —C(O)$NR_xR_y$, —$NR_xR_y$, or carboxylic acid. In some embodiments, $R_b$ represents $(C_1-C_4)$alkyl, optionally substituted with —C(O)$NH_2$, —$NH_2$, —NH(C(O)$CH_3$), or carboxylic acid; and $R_c$ represents hydrogen. In some embodiments. $R_b$ represents $(C_1-C_4)$alkyl, optionally substituted with —C(O)$NH_2$ or carboxylic acid; and $R_c$ represents hydrogen. In some embodiments, $R_b$ represents sec-butyl, —$CH_2C(O)NH_2$, —$(CH_2)_4$—$NH_2$, —$(CH_2)_4$—NH(C(O)$CH_3$), —$CH_2C(O)OH$, or —$(CH_2)_2C(O)OH$. In certain embodiments, $R_b$ represents —$CH_2C(O)NH_2$, —$(CH_2)_4$—$NH_2$, —$(CH_2)_4$—NH(C(O)$CH_3$), —$CH2C(O)OH$, or —$(CH_2)_2C(O)OH$. In certain embodiments, $R_b$ represents —$CH_2C(O)NH_2$. —$CH_2C(O)OH$, or —$(CH_2)_2C(O)OH$. In some embodiments. $R_b$ represents —$CH_2C(O)OH$ or —$(CH_2)_2C(O)OH$.

Alternatively, in certain embodiments, $R_b$ and $R_c$ taken together with the atoms to which they are attached form a 5- to 6-membered ring containing 1 to 3 heteroatoms selected from O, N or S, wherein the 5- to 6-membered ring is optionally further substituted with hydroxyl. In some embodiments, the 5- to 6-membered ring is a pyrrolidine ring, wherein the pyrrolidine ring is optionally further substituted with hydroxyl.

In some embodiments, Y represents a group represented by the following structural formula

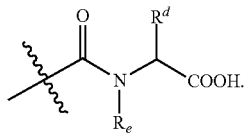

In certain embodiments, $R_d$ represents $(C_1-C_4)$alkyl, optionally substituted with —OH, —OCH$_3$, —C(O)OH, or p-OH(phenyl); and $R_e$ represents hydrogen. In certain embodiments, $R_d$ represents isopropyl, sec-butyl, —CH$_2$OH, —CH(CH$_3$)OH, —CH(CH$_3$)OCH$_3$, —CH$_2$C(O)OH, or —CH$_2$-(p-OH(phenyl)). In some embodiments, $R_d$ represents sec-butyl, —CH$_2$OH, or —CH(CH$_3$)OH. In certain embodiments, $R_d$ represents —CH(CH$_3$)OH.

Alternatively, in certain embodiments, $R_d$ and $R_e$ taken together with the atoms to which they are attached form a 5- to 6-membered ring containing 1 to 3 heteroatoms selected from O, N or S. In some embodiments, the 5- to 6-membered ring is a pyrrolidine ring.

Alternatively, in some embodiments, Y represents hydrogen.

In some embodiments of Formula (I),

Z represents —OH, or —NH-G;

G represents hydrogen or $(C_1-C_6)$alkyl;

Y represents a group represented by the following structural formula

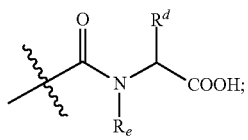

$R_a$ represents $(C_1-C_6)$alkyl substituted with —OH, —NH$_2$, carboxylic acid, guanidino, or phenyl;

$R_{a'}$ represents hydrogen; or $R_a$ and $R_{a'}$ taken together with the atom to which they are attached form a 5- to 6-membered ring, optionally containing 1 to 3 heteroatoms selected from O, N or S;

$R_b$ represents $(C_1-C_6)$alkyl, optionally substituted with —C(O)NR$_x$R$_y$ or carboxylic acid;

$R_c$ represents hydrogen; or $R_b$ and $R_c$ taken together with the atoms to which they are attached form a 5- to 6-membered ring containing 1 to 3 heteroatoms selected from O, N or S;

$R_s$ represents $(C_1-C_6)$alkyl, optionally substituted with —OR$_x$;

$R_e$ represents hydrogen; or $R_d$ and $R_e$ taken together with the atoms to which they are attached form a 5- to 6-membered ring containing 1 to 3 heteroatoms selected from O, N or S; and $R_x$ and $R_y$ independently represent hydrogen, $(C_1-C_6)$alkyl or $(C_2-C_6)$acyl.

In some embodiments of Formula (I),

Z represents —OH, or —NH-G;

G represents hydrogen or methyl;

Y represents hydrogen or a group represented by the following structural formula

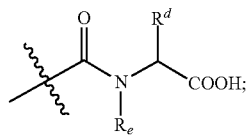

$R_a$ represents —CH$_2$OH, —CH(CH$_3$)OH, —(CH$_2$)$_4$—NH$_2$, —(CH$_2$)$_2$—SCH$_3$, —(CH$_2$)$_2$C(O)OH, —(CH$_2$)$_3$—NH—C(=NH)—NH$_2$, —CH$_2$-(phenyl), or —CH$_2$-(p-OH(phenyl)); or $R_a$ and G taken together with the atom to which they are attached form a morpholine ring;

$R_{a'}$ represents hydrogen; or $R_a$ and $R_{a'}$ taken together with the atoms to which they are attached form cyclopentyl ring;

$R_b$ represents sec-butyl, —CH$_2$C(O)NH$_2$, —(CH$_2$)$_4$—NH$_2$, —(CH$_2$)$_4$—NH(C(O)CH$_3$), —CH$_2$C(O)OH, or —(CH$_2$)$_2$C(O)OH;

$R_c$ represents hydrogen; or $R_b$ and $R_c$ taken together with the atoms to which they are attached to form a pyrrolidine ring, wherein the pyrrolidine ring is optionally further substituted with hydroxyl;

$R_d$ represents isopropyl, sec-butyl, —CH$_2$OH, —CH(CH$_3$)OH, —CH(CH$_3$)OCH$_3$, —CH$_2$C(O)OH, or —CH$_2$-(p-OH(phenyl)); and $R_e$ represents hydrogen; or $R_d$ and $R_e$ taken together with the atoms to which they are attached to form a pyrrolidine ring.

In certain embodiments of Formula (I),

Z represents —OH, or —NH-G;

G represents hydrogen or methyl;

Y represents a group represented by the following structural formula

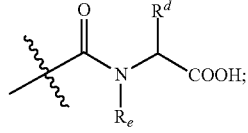

$R_a$ represents —CH$_2$OH, —CH(CH$_3$)OH, —(CH$_2$)$_4$—NH$_2$, —(CH$_2$)$_2$C(O)OH, —(CH$_2$)$_3$—NH—C(=NH)—NH$_2$, or —CH$_2$-(phenyl);

$R_{a'}$ represents hydrogen;

$R_b$ represents —CH$_2$C(O)NH$_2$, —CH$_2$C(O)OH, or —(CH$_2$)$_2$C(O)OH;

$R_c$ represents hydrogen; or $R_b$ and $R_c$ taken together with the atoms to which they are attached to form a pyrrolidine ring;

$R_d$ represents sec-butyl, —CH$_2$OH, or —CH(CH$_3$)OH; and $R_e$ represents hydrogen.

In certain embodiments, $R_a$ represents —CH$_2$OH, —CH(CH$_3$)OH, or —(CH$_2$)$_3$—NH—C(=NH)—NH$_2$; $R_b$ represents —CH$_2$C(O)NH$_2$, —CH$_2$C(O)OH, or —(CH$_2$)$_2$C(O)OH; and $R_d$ represents —CH$_2$OH or —CH(CH$_3$)OH. In some embodiments, $R_a$ represents —CH$_2$OH or —CH(CH$_3$)OH; $R_b$ represents —CH$_2$C(O)OH or —(CH$_2$)$_2$C(O)OH; and $R_d$ represents —CH(CH$_3$)OH. In some embodiments, $R_a$ represents —CH$_2$OH; $R_b$ represents —CH$_2$C(O)OH or —(CH$_2$)$_2$C(O)OH; and $R_d$ represents —CH(CH$_3$)OH. In some embodiments, $R_a$ represents —CH(CH$_3$)OH; $R_b$ represents —CH$_2$C(O)NH$_2$; and $R_d$ represents —CH$_2$OH. In some embodiments, $R_a$ represents —(CH$_2$)$_3$—NH—C(=NH)—NH$_2$; $R_b$ represents —CH$_2$C(O)NH$_2$; and $R_d$ represents —CH$_2$OH.

In certain embodiments of the methods and compositions disclosed herein, the compound, or a pharmaceutically acceptable salt thereof, is selected from:

TABLE 1

| Compd No. | Z | G | $R_a$ | $R_{a'}$ | $R_b$ | $R_c$ | $R_d$ | $R_e$ |
|---|---|---|---|---|---|---|---|---|
| 1 | —NH—G | H | —(CH$_2$)$_2$C(O)OH<br>Glu E | H | —CH$_2$C(O)NH$_2$<br>Asn N | H | —CH(CH$_3$)OH<br>Thr T | H |
| 2 | —NH—G | H | —CH$_2$OH<br>Ser S | H | —CH$_2$C(O)NH$_2$<br>Asn N | H | sec-butyl<br>Ile I | H |
| 3 | —NH—G | H | —CH$_2$-(phenyl)<br>Phe F | H | —CH$_2$C(O)NH$_2$<br>Asn N | H | —CH(CH$_3$)OH<br>Thr T | H |
| 4 | —NH—G | H | —CH$_2$OH<br>Ser S | H | —CH$_2$C(O)OH<br>Asp D | H | —CH(CH$_3$)OH<br>Thr T | H |
| 5 | —NH—G | H | —CH$_2$OH<br>Ser S | H | —(CH$_2$)$_2$C(O)OH<br>Glu E | H | —CH(CH$_3$)OH<br>Thr T | H |
| 6 | —NH—G | H | —(CH$_2$)$_4$—NH$_2$<br>Lys K | H | —(CH$_2$)$_2$C(O)OH<br>Glu E | H | —CH(CH$_3$)OH<br>Thr T | H |
| 7 | —NH—G | H | —CH$_2$OH<br>Ser S | H | —CH$_2$C(O)NH$_2$<br>D-Asn n | H | —CH(CH$_3$)OH<br>Thr T | H |
| 8 | —NH—G | H | —CH(CH$_3$)OH<br>D-Thr t | H | —CH$_2$C(O)NH$_2$<br>D-Asn n | H | —CH$_2$OH<br>D-Ser s | H |
| 9 | —NH—G | H | —(CH$_2$)$_4$—NH$_2$<br>Lys K | H | —CH$_2$C(O)NH$_2$<br>Asn N | H | isopropyl<br>Val V | H |
| 10 | —NH—G | H | —(CH$_2$)$_2$SCH$_3$<br>Met M | H | —CH$_2$C(O)NH$_2$<br>Asn N | H | —CH$_2$C(O)OH<br>Asp D | H |
| 11 | —NH—G | H | —(CH$_2$)$_4$—NH$_2$<br>Lys K | H | —(CH$_2$)$_2$C(O)OH<br>Glu E | H | —CH$_2$OH<br>Ser S | H |
| 12 | —NH—G | H | (CH$_2$)$_4$—NH$_2$<br>Lys K | H | —CH$_2$C(O)NH$_2$<br>Asn N | H | —CH$_2$OH<br>Ser S | H |
| 13 | —NH—G | H | —CH$_2$OH<br>Ser S | H | —(CH$_2$)$_4$—NH$_2$<br>Lys K | H | —CH(CH$_3$)OH<br>Thr T | H |
| 14 | —NH—G | H | —CH$_2$OH<br>Ser S | H | —CH$_2$C(O)NH$_2$<br>Asn N | H | —CH(CH$_3$)OMe<br>Thr T(OMe) | H |
| 15 | —NH—G | H | —CH$_2$OH<br>Ser S | H | sec-butyl<br>Ile I | H | —CH(CH$_3$)OH<br>Thr T | H |
| 16 | —NH—G | | Morpholine | | —CH$_2$C(O)NH$_2$<br>Asn N | H | —CH(CH$_3$)OH<br>Thr T | H |
| 17 | —NH—G | | Morpholine | | (CH$_2$)$_2$C(O)OH<br>Glu E | H | —CH(CH$_3$)OH<br>Thr T | H |
| 18 | —NH—G | H | —CH$_2$-(p-OH(phenyl))<br>Tyr Y | H | -(4-OH-(pyrrolidine ring))<br>Hydroxy-Pro | | —CH$_2$-(p-OH(phenyl))<br>Tyr Y | H |
| 19 | —NH—G | H | —CH$_2$-(p-OH(phenyl))<br>Tyr Y | H | -(piperidine) | | —CH$_2$-(p-OH(phenyl))<br>Tyr Y | H |
| 20 | —NH—G | H | —CH$_2$OH<br>Ser S | H | —(CH$_2$)$_4$—NH(C(O)CH$_3$)<br>Lys K(acyl) | H | —CH(CH$_3$)OH<br>Thr T | H |
| 21 | —NH—G | H | —CH$_2$-p-OH(phenyl))<br>Tyr Y | H | —CH$_2$C(O)NH$_2$<br>Asn N | H | —CH(CH$_3$)OH<br>Thr T | H |
| 22 | —NH—G | H | —CH$_2$OH<br>Ser S | H | —CH$_2$C(O)NH$_2$<br>Asn N | H | —CH(CH$_3$)OH<br>D-Thr t | H |
| 23 | —NH—G | H | Cyclopentyl ring | | H—CH$_2$C(O)NH$_2$<br>Asn N | H | —CH(CH$_3$)OH<br>Thr T | H |
| 24 | —OH | — | —CH$_2$OH<br>Ser S | H | —CH$_2$C(O)NH$_2$<br>Asn N | H | —CH(CH$_3$)OH<br>Thr T | H |
| 25 | —NH—G | H | —(CH$_2$)$_3$—NH—C(=NH)—NH$_2$<br>Arg R | H | —CH$_2$C(O)NH$_2$<br>Asn N | H | —CH$_2$OH<br>Scr S | H |
| 26 | —NH—G | CH$_3$ | —CH$_2$OH<br>Ser S | H | —CH$_2$C(O)NH$_2$<br>Asn N | H | — | — |

In some embodiments of the methods and compositions disclosed herein, the compound, or a pharmaceutically acceptable salt thereof, is selected from:

TABLE 2

| Compd No. | Z | G | $R_a$ | $R_{a'}$ | $R_b$ | $R_c$ | $R_d$ | $R_e$ |
|---|---|---|---|---|---|---|---|---|
| 1 | —NH—G | H | —(CH$_2$)$_2$C(O)OH<br>Glu E | H | —CH$_2$C(O)NH$_2$<br>Asn N | H | —CH(CH$_3$)OH<br>Thr T | H |
| 2 | —NH—G | H | —CH$_2$OH<br>Ser S | H | —CH$_2$C(O)NH$_2$<br>Asn N | H | sec-butyl<br>Ile I | H |
| 3 | —NH—G | H | —CH$_2$-(phenyl)<br>Phe F | H | —CH$_2$C(O)NH$_2$<br>Asn N | H | —CH(CH$_3$)OH<br>Thr T | H |

TABLE 2-continued

| Compd No. | Z | G | $R_a$ | $R_{a'}$ | $R_b$ | $R_c$ | $R_d$ | $R_e$ |
|---|---|---|---|---|---|---|---|---|
| 4 | —NH—G | H | —CH$_2$OH<br>Ser S | H | —CH$_2$C(O)OH<br>Asp D | H | —CH(CH$_3$)OH<br>Thr T | H |
| 5 | —NH—G | H | —CH$_2$OH<br>Ser S | H | —(CH$_2$)$_2$C(O)OH<br>Glu E | H | —CH(CH$_3$)OH<br>Thr T | H |
| 6 | —NH—G | H | —(CH$_2$)$_4$—NH$_2$<br>Lys K | H | —(CH$_2$)$_2$C(O)OH<br>Glu E | H | —CH(CH$_3$)OH<br>Thr T | H |
| 7 | —NH—G | H | —CH$_2$OH<br>Ser S | H | —CH$_2$C(O)NH$_2$<br>D-Asn n | H | —CH(CH$_3$)OH<br>Thr T | H |
| 8 | —NH—G | H | —CH(CH$_3$)OH<br>D-Thr t | H | —CH$_2$C(O)NH$_2$<br>D-Asn n | H | —CH$_2$OH<br>D-Ser s | H |
| 9 | —NH—G | H | —(CH$_2$)$_4$—NH$_2$<br>Lys K | H | —CH$_2$C(O)NH$_2$<br>Asn N | H | isopropyl<br>Val V | H |
| 10 | —NH—G | H | —(CH$_2$)$_2$SCH$_3$<br>Met M | H | —CH$_2$C(O)NH$_2$<br>Asn N | H | —CH$_2$C(O)OH<br>Asp D | H |
| 11 | —NH—G | H | —(CH$_2$)$_4$—NH$_2$<br>Lys K | H | (CH$_2$)$_2$C(O)OH<br>Glu E | H | —CH$_2$OH<br>Ser S | H |
| 12 | —NH—G | H | —(CH$_2$)$_4$—NH$_2$<br>Lys K | H | —CH$_2$C(O)NH$_2$<br>Asn N | H | —CH$_2$OH<br>Ser S | H |
| 13 | —NH—G | H | —CH$_2$OH<br>Ser S | H | —(CH$_2$)$_4$—NH$_2$<br>Lys K | H | —CH(CH$_3$)OH<br>Thr T | H |
| 14 | —NH—G | H | —CH$_2$OH<br>Ser S | H | —CH$_2$C(O)NH$_2$<br>Asn N | H | —CH(CH$_3$)OMe<br>Thr T(OMe) | H |
| 16 | —NH—G |   | Morpholine |   | —CH$_2$C(O)NH$_2$<br>Asn N |   | —CH(CH$_3$)OH<br>Thr T | H |
| 17 | —NH—G |   | Morpholine |   | —(CH$_2$)$_2$C(O)OH<br>Glu E |   | —CH(CH$_3$)OH<br>Thr T | H |
| 18 | —NH—G | H | —CH$_2$-(p-OH(phenyl))<br>Tyr Y | H | -(4-OH-(pyrrolidine ring))Hydroxy-Pro |   | —CH$_2$-(p-OH(phenyl))<br>Tyr Y | H |
| 19 | —NH—G | H | —CH$_2$-(p-OH(phenyl))<br>Tyr Y | H | -(piperidine) |   | —CH$_2$-(p-OH(phenyl))<br>Tyr Y | H |
| 20 | —NH—G | H | —CH$_2$OH<br>Ser S | H | —(CH$_2$)$_4$—NH(C(O)CH$_3$)<br>Lys K(acyl) | H | —CH(CH$_3$)OH<br>Thr T | H |
| 24 | —OH | — | —CH$_2$OH<br>Ser S | H | —CH$_2$C(O)NH$_2$<br>Asn N | H | —CH(CH$_3$)OH<br>Thr T | H |
| 25 | —NH—G | H | —(CH$_2$)$_3$—NH—C(=NH)—NH$_2$<br>Arg R | H | —CH$_2$C(O)NH$_2$<br>Asn N | H | —CH$_2$OH<br>Ser S | H |
| 26 | —NH—G | CH$_3$ | —CH$_2$OH<br>Ser S | H | —CH$_2$C(O)NH$_2$<br>Asn N | H | — | — |

In some embodiments of the methods and compositions disclosed herein, the compound, or a pharmaceutically acceptable salt thereof, is selected from:

TABLE 3

| Compd No. | Z | G | $R_a$ | $R_{a'}$ | $R_b$ | $R_c$ | $R_d$ | $R_e$ |
|---|---|---|---|---|---|---|---|---|
| 1 | —NH—G | H | —(CH$_2$)$_2$C(O)OH<br>Glu E | H | —CH$_2$C(O)NH$_2$<br>Asn N | H | —CH(CH$_3$)OH<br>Thr T | H |
| 2 | —NH—G | H | —CH$_2$OH<br>Ser S | H | —CH$_2$C(O)NH$_2$<br>Asn N | H | sec-butyl<br>Ile I | H |
| 3 | —NH—G | H | —CH$_2$-(phenyl)<br>Phe F | H | —CH$_2$C(O)NH$_2$<br>Asn N | H | —CH(CH$_3$)OH<br>Thr T | H |
| 4 | —NH—G | H | —CH$_2$OH<br>Ser S | H | —CH$_2$C(O)OH<br>Asp D | H | —CH(CH$_3$)OH<br>Thr T | H |
| 5 | —NH—G | H | —CH$_2$OH<br>Ser S | H | —(CH$_2$)$_2$C(O)OH<br>Glu E | H | —CH(CH$_3$)OH<br>Thr T | H |
| 6 | —NH—G | H | —(CH$_2$)$_4$—NH$_2$<br>Lys K | H | —(CH$_2$)$_2$C(O)OH<br>Glu E | H | —CH(CH$_3$)OH<br>Thr T | H |
| 7 | —NH—G | H | —CH$_2$OH<br>Ser S | H | CH$_2$C(O)NH$_2$<br>D-Asn n | H | —CH(CH$_3$)OH<br>Thr T | H |
| 8 | —NH—G | H | —CH(CH$_3$)OH<br>D-Thr t | H | CH$_2$C(O)NH$_2$<br>D-Asn n | H | —CH$_2$OH<br>D-Ser s | H |
| 24 | —OH | — | —CH$_2$OH<br>Ser S | H | —CH$_2$C(O)NH$_2$<br>Asn N | H | —CH(CH$_3$)OH<br>Thr T | H |
| 25 | —NH—G | H | —(CH$_2$)$_3$—NH—C(=NH)—NH$_2$<br>Arg R | H | —CH$_2$C(O)NH$_2$<br>Asn N | H | —CH$_2$OH<br>Ser S | H |

In certain embodiments of the methods and compositions disclosed herein, the compound, or a pharmaceutically acceptable salt thereof, is selected from:

TABLE 4

| Compound No. | Structure |
|---|---|
| 1 | 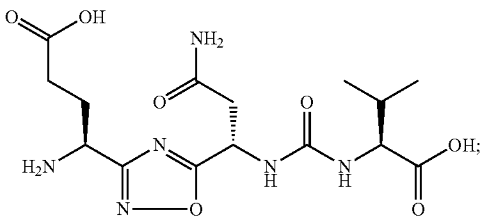 [SMILES: CC(C)[C@H](NC(=O)N[C@@H](CC(N)=O)c1nc([C@@H](N)CCC(=O)O)no1)C(=O)O] |
| 2 | 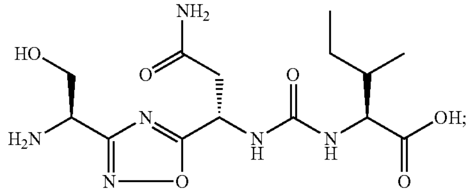 [SMILES: CCC(C)[C@H](NC(=O)N[C@@H](CC(N)=O)c1nc([C@@H](N)CO)no1)C(=O)O] |
| 3 | 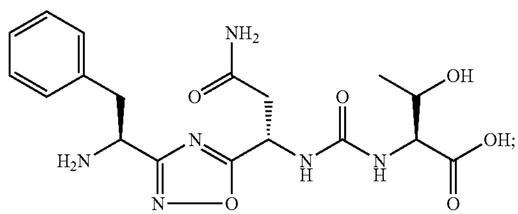 [SMILES: CC(O)[C@H](NC(=O)N[C@@H](CC(N)=O)c1nc([C@@H](N)Cc2ccccc2)no1)C(=O)O] |
| 4 | 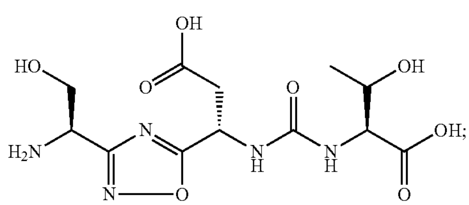 [SMILES: CC(O)[C@H](NC(=O)N[C@@H](CC(=O)O)c1nc([C@@H](N)CO)no1)C(=O)O] |
| 5 | 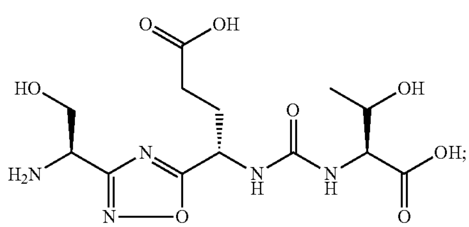 [SMILES: CC(O)[C@H](NC(=O)N[C@@H](CCC(=O)O)c1nc([C@@H](N)CO)no1)C(=O)O] |
| 6 | 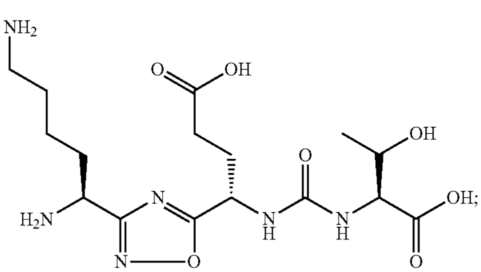 [SMILES: CC(O)[C@H](NC(=O)N[C@@H](CCC(=O)O)c1nc([C@@H](N)CCCCN)no1)C(=O)O] |

TABLE 4-continued

| Compound No. | Structure |
|---|---|
| 7 | (structure) |
| 8 | (structure) |
| 9 | (structure) |
| 10 | (structure) |
| 11 | (structure) |
| 12 | (structure) |

TABLE 4-continued
| Compound No. | Structure |
|---|---|
| 13 | 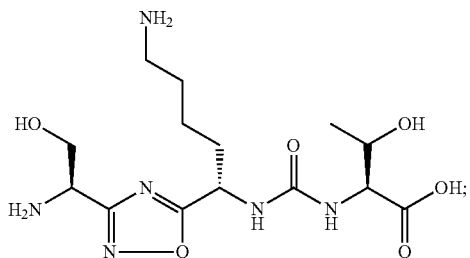 [SMILES: CC(O)[C@H](NC(=O)N[C@@H](CCCCN)c1nc([C@@H](N)CO)no1)C(=O)O] |
| 14 | 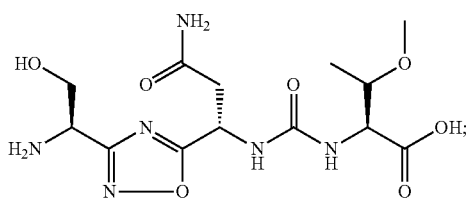 [SMILES: COC(C)[C@H](NC(=O)N[C@@H](CC(N)=O)c1nc([C@@H](N)CO)no1)C(=O)O] |
| 15 | 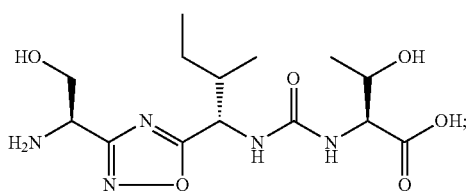 [SMILES: CCC(C)[C@H](NC(=O)N[C@H](C(=O)O)C(C)O)c1nc([C@@H](N)CO)no1] |
| 16 | 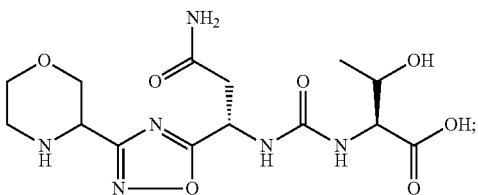 [SMILES: CC(O)[C@H](NC(=O)N[C@@H](CC(N)=O)c1nc(C2COCCN2)no1)C(=O)O] |
| 17 | 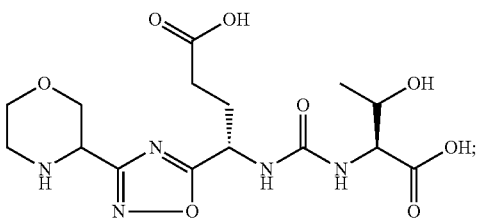 [SMILES: CC(O)[C@H](NC(=O)N[C@@H](CCC(=O)O)c1nc(C2COCCN2)no1)C(=O)O] |
| 18 | 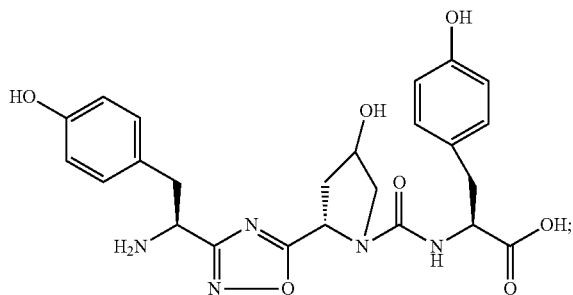 |

TABLE 4-continued

| Compound No. | Structure |
| --- | --- |
| 19 | 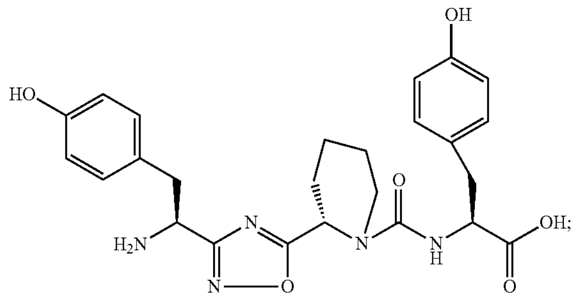 [SMILES: N[C@@H](Cc1ccc(O)cc1)c1noc([C@@H]2CCCCN2C(=O)N[C@@H](Cc2ccc(O)cc2)C(=O)O)n1] |
| 20 | 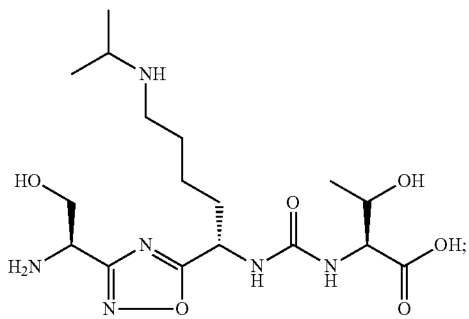 [SMILES: CC(C)NCCCC[C@H](NC(=O)N[C@H](C(=O)O)C(C)O)c1nc([C@@H](N)CO)no1] |
| 21 | 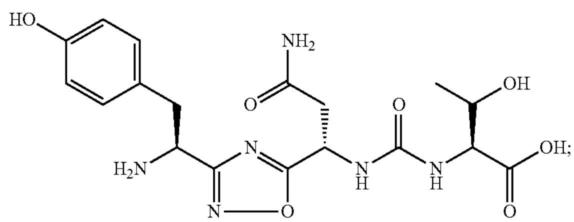 [SMILES: CC(O)[C@H](NC(=O)N[C@@H](CC(N)=O)c1nc([C@@H](N)Cc2ccc(O)cc2)no1)C(=O)O] |
| 22 | 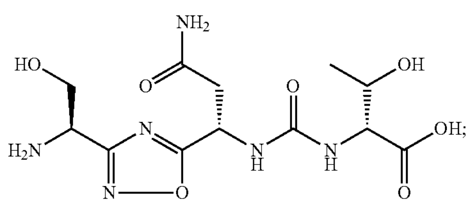 [SMILES: CC(O)[C@@H](NC(=O)N[C@@H](CC(N)=O)c1nc([C@@H](N)CO)no1)C(=O)O] |
| 23 | 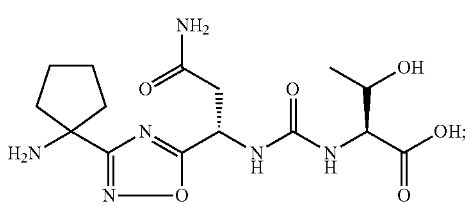 [SMILES: CC(O)[C@H](NC(=O)N[C@@H](CC(N)=O)c1nc(C2(N)CCCC2)no1)C(=O)O] |
| 24 | 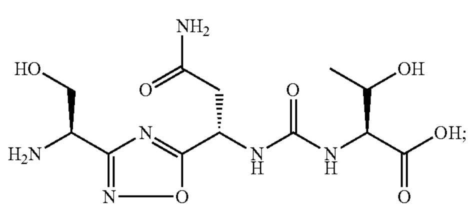 |

TABLE 4-continued

| Compound No. | Structure |
|---|---|
| 25 | [Structure: Arginine-containing compound with oxadiazole ring linked via urea to serine] and |
| 26 | [Structure: N-methyl serine-oxadiazole-asparagine derivative with NH₂] |

In certain embodiments of the methods and compositions disclosed herein, the compound, or a pharmaceutically acceptable salt thereof, is selected from:

TABLE 5

| Compound No. | Structure |
|---|---|
| 1 | [Structure: Glutamic acid-oxadiazole-asparagine-urea-threonine derivative] |
| 2 | [Structure: Serine-oxadiazole-asparagine-urea-isoleucine derivative] |
| 3 | [Structure: Phenylalanine-oxadiazole-asparagine-urea-threonine derivative] |
| 4 | [Structure: Serine-oxadiazole-aspartic acid-urea-threonine derivative] |

TABLE 5-continued

| Compound No. | Structure |
|---|---|
| 5 | (structure) |
| 6 | (structure) |
| 7 | (structure) |
| 8 | (structure) |
| 9 | (structure) |
| 10 | (structure) |

TABLE 5-continued

| Compound No. | Structure |
| --- | --- |
| 11 | (chemical structure) |
| 12 | (chemical structure) |
| 13 | (chemical structure) |
| 14 | (chemical structure) |
| 16 | (chemical structure) |
| 17 | (chemical structure) |

TABLE 5-continued

| Compound No. | Structure |
|---|---|
| 18 | (structure) |
| 19 | (structure) |
| 20 | (structure) |
| 24 | (structure); and |
| 25 | (structure). |

In certain embodiments of the methods and compositions disclosed herein, $R_a$ represents a side chain of an amino acid residue. In some embodiments, $R_b$ represents a side chain of an amino acid residue. In some embodiments, $R_d$ represents a side chain of an amino acid residue. In certain embodiments, $R_a$, $R_b$, and $R_d$ each represent a side chain of an amino acid residue.

An amino acid residue is understood in the art to mean a carboxylic acid, substituted at the alpha, beta, or gamma carbon by an amino (—NH$_2$) group. In the group —CO-Aaa, the amino acid residue Aaa is connected to the carbonyl group CO via a covalent bond between the carbonyl carbon and the amino group of the amino acid residue. In preferred embodiments, the amino acid is an alpha-amino acid, and the amino acid residue Aaa is connected to the carbonyl group CO via a covalent bond between the carbonyl carbon and the alpha-amino group of the amino acid residue.

In accordance with any of the foregoing embodiments, in certain embodiments. one, more than one, or all amino acid residues are D amino acid residues. In some embodiments, one, more than one, or all amino acid residue side chains correspond to the stereochemistry of D amino acid residues.

In certain embodiments, one, more than one, or all amino acid residues are L amino acid residues. In some embodiments, one, more than one, or all amino acid residue side chains correspond to the stereochemistry of L amino acid residues.

In certain embodiments of the methods and compositions disclosed herein, the compounds may be prodrugs of the compounds of Formula (I), e.g., wherein a hydroxyl in the parent compound is presented as an ester or a carbonate, or carboxylic acid present in the parent compound is presented as an ester. In a further embodiment, the prodrug is metabolized to the active parent compound in vivo (e.g., the ester is hydrolyzed to the corresponding hydroxyl, or carboxylic acid).

In certain embodiments of the methods and compositions disclosed herein, the compounds of the present disclosure can also contain unnatural proportions of atomic isotopes at one or more of the atoms that constitute such compounds. For example, the present disclosure also embraces isotopically-labeled variants of the present disclosure which are identical to those recited herein, but for the fact that one or more atoms of the compound are replaced by an atom having the atomic mass or mass number different from the predominant atomic mass or mass number usually found in nature for the atom.

All isotopes of any particular atom or element as specified are contemplated within the scope of the compounds of the disclosure, and their uses. Exemplary isotopes that can be incorporated in to compounds of the disclosure include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, 15O, $^{17}$O, $^{18}$O, $^{35}$S, $^{18}$F, $^{36}$Cl, $^{123}$I and $^{125}$I. Isotopically labeled compounds of the present disclosures can generally be prepared by following procedures analogous to those disclosed in the schemes and/or in the examples herein below, by substituting an isotopically labeled reagent for a non-isotopically labeled reagent.

In some embodiments of the methods disclosed herein, the immune response is further mediated by the programmed cell death 1 (PD-1) signaling pathway.

In some embodiments of the methods disclosed herein, the immune response is further mediated by a TIM-3 agent. In some embodiments, the TIM-3 agent is selected from galectin-9, carcinoembryonic antigen related cell adhesion molecule 1 (CEACAM1), high-mobility group box 1 (HMGB1), phosphatidyl serine, leukocyte immunoglobulin-like receptor A3 (LILRA3), and leukocyte immunoglobulin-like receptor B2 (LILRB2).

In some embodiments of the methods disclosed hercin, the immune response is further mediated by a group 1 leukocyte immunoglobulin-like receptor (LILR) family protein, including the inhibitory LILRB1 and LILRB2 and the activating LILRA1, LILRA2, and LILRA3 receptors. In some embodiments, the immune response is further mediated by LILRA3, a chimeric protein (e.g., LILRA3-Fc), a functional variant thereof, or a fragment thereof.

Methods of Use

In some embodiments, the present disclosure provides a method of modulating an immune response mediated by TIM-3 activity in a cell, comprising contacting the cell with a compound of Formula (I), or a pharmaceutically acceptable salt thereof, according to any of the above embodiments. In some embodiments, the present disclosure provides a method of modulating an immune response mediated by the PD-1 pathway (e.g., PD-1. PD-L1, or PD-L2) and TIM-3 activity in a cell, comprising contacting the cell with a compound of Formula (I), or a pharmaceutically acceptable salt thereof, according to any of the above embodiments.

In certain embodiments, the present disclosure provides uses of a compound of Formula (I) for the preparation of a medicament for the treatment of a TIM-3-mediated disorder, disease, or condition. In some embodiments, the present disclosure provides uses of a compound of Formula (I) in the manufacture of a medicament, e.g., for the treatment of cancer, immune disorders, immunodeficiency disorders, inflammatory disorders, infectious diseases, and transplant rejection.

In accordance with any of the foregoing embodiments, in certain embodiments, contacting the cell occurs in a subject in need thereof, thereby treating a disease or disorder selected from cancer, immune disorders, immunodeficiency disorders, inflammatory disorders, infectious diseases, and transplant rejection.

In accordance with any of the foregoing embodiments, in some embodiments, contacting the cell occurs in a subject in need thereof, thereby treating a disease or disorder, wherein the cell is selected from a cancer cell, a cancer stem cell, and an immune cell.

Some embodiments of the present disclosure provide a method of treatment of cancer by inhibition of TIM-3.

Certain embodiments of the present disclosure provide a method of treatment of cancer by blockade of the PD-1 pathway and inhibition of TIM-3, for example inhibiting an immunosuppressive signal induced by PD-1, PD-L1, or PD-L2 and/or TIM-3, wherein the method comprises administration of a therapeutically effective amount of a compound of Formula (I) to the subject in need thereof.

Some embodiments of the present disclosure provide a method of treatment of cancer by inhibition of an immune regulatory pathway or an immune checkpoint pathway.

In certain embodiments, the present disclosure provides uses of a compound of the present disclosure for the preparation of a medicament for the treatment of cancer.

In certain embodiments, the present disclosure provides methods for treating cancer, wherein the method comprises administration of a therapeutically effective amount of a compound of Formula (I) to the subject in need thereof.

In certain embodiments, the present disclosure provides methods for inhibiting growth of tumor cells and/or metastasis by administering a therapeutically effective amount of a compound of Formula (I) to the subject in need thereof.

Representative tumor cells include cells of a cancer such as, but not limited to, blastoma (e.g., glioblastoma and glioblastoma multiforme), breast cancer (e.g., breast carcinoma, breast invasive carcinoma, primary ductal carcinoma, triple negative breast cancer, estrogen receptor positive (ER+), progesterone receptor positive (PR+), and/or human epidermal growth factor receptor 2 positive (HER2+)), epithelial cancer (e.g., carcinomas and basal cell carcinoma), lung cancer (e.g., small cell lung cancer, non-small cell lung cancer (NSCLC), lung adenocarcinoma, and lung squamous cell carcinoma), melanoma (e.g., cutaneous melanoma, skin cutaneous melanoma, ocular melanoma, cutaneous or intraocular malignant melanoma, uveal melanoma, and lymph node-associated melanoma), prostate cancer (e.g., prostate adenocarcinoma), renal cancer (e.g., renal cell cancer (RCC), kidney cancer, kidney renal clear cell carcinoma, kidney renal papillary cell carcinoma, kidney chromophobe, and Wilms tumor), bone cancer (e.g., osteosarcoma), pancreatic cancer (e.g., pancreatic adenocarcinoma), skin cancer, cancer of the head or neck (e.g., head and neck squamous cell carcinoma), uterine cancer (e.g., choriocarcinoma, uterine carcinosarcoma, and uterine corpus endometrial carcinoma), ovarian cancer (e.g., ovarian carcinoma), colorectal cancer (e.g., microsatellite instability high colorectal cancer and colorectal adenocarcinoma), rectal cancer (e.g., rectum adenocarcinoma), cancer of the anal region, cancer of the peritoneum, connective tissue cancer, eye cancer (e.g., retinoblastoma), throat cancer (e.g., laryngeal cancer), oral cavity cancer (e.g., lip cancer, tongue cancer, mouth cancer, pharyngeal cancer, and salivary gland cancer), biliary tract cancer (e.g., cholangiocarcinoma), stomach cancer (e.g., gastric carcinoma, stomach adenocarcinoma, and gastrointestinal cancer), testicular cancer (e.g., testicular germ cell tumor). carcinoma of the fallopian tubes, endometrial cancer (e.g., carcinoma of the endometrium), cervical cancer (e.g., carcinoma of the cervix, cervical intraepithelial neoplasia, cervical squamous cell carcinoma, and endocervical adenocarcinoma), vaginal cancer (e.g., carcinoma of the vagina), vulval cancer (e.g., carcinoma of the vulva), cancer of the esophagus (e.g., esophageal cancer), cancer of the small intestine, cancer of the endocrine system, thyroid cancer (e.g., cancer of the thyroid gland and thyroid carcinoma), cancer of the parathyroid gland, cancer of the adrenal gland (e.g., adrenocortical cancer and pheochromocytoma), sarcoma (e.g., sarcoma of soft tissue. Kaposi's sarcoma, and rhabdomyosarcoma), cancer of the urethra, cancer of the penis, chronic or acute leukemia (e.g., acute myeloid leukemia, chronic myeloid leukemia. acute lymphoblastic leukemia, chronic lymphocytic leukemia, Hairy cell leukemia, and chronic myeloblastic leukemia), solid tumors of childhood, Hodgkin's lymphoma (HL) (e.g., lymphocyte-rich (LRCHL), nodular sclerosis (NSHL), mixed cellularity (MCHL) and lymphocyte depleted (LDHL)), B-cell lymphomas (e.g., diffuse large B-cell lymphoma (DLBCL) and lymphoid neoplasm DLBCL), non-Hodgkin's lymphoma (NHL) (e.g., low grade/follicular non-Hodgkin's lymphoma, small lymphocytic (SL)

NHL, intermediate grade/follicular NHL, intermediate grade diffuse NHL, high grade immunoblastic NHL, high grade lymphoblastic NHL, high grade small non-cleaved cell NHL, bulky disease NHL. Burkitt's lymphoma, mantle cell lymphoma), AIDS-related lymphoma, cutaneous T-cell lymphoma (e.g., mycosis fundoides) and Waldenstrom's Macroglobulinemia, post-transplant lymphoproliferative disorder (PTLD), lymphocytic lymphoma, primary CNS lymphoma, and T-cell lymphoma), acute lymphocytic leukemia (ALL), acute myeloid leukemia (AML), chronic lymphocytic leukemia (CLL), chronic myelogenous leukemia (CML), myeloproliferative disorder/neoplasm (MPDS). myelodysplasia syndrome, a monocytic leukemia, a B-cell derived leukemia, a T-cell derived leukemia, solid tumors of childhood, a B-cell derived lymphoma, T-cell derived lymphoma, Hodgkin's lymphoma, indolent and aggressive non-Hodgkin's lymphoma, Burkitt's lymphoma, follicular lymphoma (small cell and large cell), mesothelioma, thymic carcinoma, thymoma, myeloma (e.g., multiple myeloma, giant cell myeloma, heavy-chain myeloma, and light chain or Bence-Jones myeloma), a mast cell derived tumor, leiomyoma, leiomyosarcoma, glioma (e.g., brain lower grade glioma and paraganglioma), cancer of the bladder (e.g., bladder carcinoma and bladder urothelial carcinoma), cancer of the ureter, carcinoma of the renal pelvis, liver cancer (e.g., hepatocellular cancer, hepatic carcinoma, hepatoma), pancreatic cancer (e.g., pancreatic adenocarcinoma), post-transplant lymphoproliferative disorder (PTLD), neuroblastic-derived CNS tumors, neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, environmentally induced cancers (including those induced by asbestos), and combinations of said cancers.

In some embodiments, for example, the tumor cells may include cells of a cancer selected from breast cancer, colon cancer, liver cancer, ovarian cancer, prostate cancer, renal cancer, a sarcoma, or uterine cancer. In some embodiments, for example, the tumor cells may include cells of a cancer selected from ovarian cancer, colon cancer, breast cancer, lung cancer, head and neck cancer, bladder cancer, melanoma, colorectal cancer, pancreatic cancer, leiomyoma, leiomyosarcoma, osteosarcoma, glioma, glioblastoma, solid tumors (e.g., breast tumors, ovarian tumors, uterine tumors, lung tumors, pancreatic tumors, prostate tumors, melanoma tumors, colon tumors, colorectal tumors, head and neck tumors, bladder tumors, esophageal tumors, liver tumors, and kidney tumors), a myeloma (e.g., multiple myeloma (MM)), a neuroblastic-derived CNS tumor, a leukemia (e.g., a monocytic leukemia, a B-cell derived leukemia, a T-cell derived leukemia, acute lymphocytic leukemia (ALL), acute myeloid leukemia (AML), chronic lymphocytic leukemia (CLL), chronic myelogenous leukemia (CML)), a lymphoma (e.g., a B-cell derived lymphoma, a T-cell derived lymphoma, and non-Hodgkin's lymphoma (NHL)), a mast cell derived tumor, and combinations of said cancers.

In some embodiments, for example, the tumor cells are from a hematopoietic cancer. In some embodiments, the hematopoietic cancer is selected from a lymphoma (e.g., B cell lymophoma, T cell lymphoma, Burkitt's lymphoma, follicular lymphoma (small cell and large cell), Hodgkin's lymphoma, or non-Hodgkin's lymphoma), a leukemia (e.g., acute myelogenous leukemia (AML), acute lymphoblastic leukemia (ALL), chronic myelogenous leukemia (CML), chronic lymphoblastic leukemia (CLL), chronic myelo-monocytic leukemia (CMML), myeloproliferative disorder/neoplasm (MPDS), and myelodysplastic syndrome (MDS)), and myeloma (e.g., multiple myeloma, heavy-chain myeloma, light chain or Bence-Jones myeloma, and plasmacytoma). In some embodiments, the hematopoietic cancer is AML. In some embodiments, the hematopoietic cancer is B cell lymophoma.

In some embodiments, the tumor cells are, and/or the subject is, naïve to immunooncology therapy. Immunooncology uses the subject's immune system to help fight cancer. For example, an immunooncology therapy includes, but is not limited to, atezolizumab (human monoclonal antibody that targets PD-L1), avelumab (human monoclonal antibody that targets PD-L1), brentuximab vedotin (antibody-drug conjugate that targets CD30), rituximab (antibody that targets CD20), durvalamab (human monoclonal antibody that targets PD-L1), ipilimumab (human monoclonal antibody that targets CTLA-4), nivolumab (human monoclonal antibody that targets PD-L1), pembrolizumab (also referred to as lambrolizumab, human monoclonal antibody that targets PD-L1), tremelimumab (human monoclonal antibody that targets CTLA-4), CT-011 (antibody that targets PD-1), MDX-1106 (antibody that targets PD-1). MK-3475 (antibody that targets PD-1), YW243.55.S70 (antibody that targets PD-L1), MPDL3280A(antibody that targets PD-L1), MDX-1105 (antibody that targets PD-L1), and MEDI4736 (antibody that targets PD-L1). In some embodiments, the immunooncology therapy is selected from an anti-CTLA-4 antibody, an anti-PD-1 antibody, an anti-PD-L1 antibody, an anti-PD-L2 antibody, an anti-LAG3 antibody, an anti-TIGIT antibody (e.g., antibodies disclosed in WO 2015/009856), and an anti-TIM-3 antibody (e.g., antibodies disclosed in US 2016/021005).

In some embodiments, a biological sample comprises tumor cells of a cancer where response to immune checkpoint therapy has been demonstrated, either by testing of a sampling of representative tumors of that type, or by testing a patient's own tumor. In some embodiments, the cancer has shown response to anti-PD1 therapy, e.g., by testing of a sampling of representative tumors of that type. For example, the cancer may include non-small cell lung cancer (NSCLC), melanoma, renal cell cancer (RCC), cancer of the bladder, Hodgkin's lymphoma, and head and neck squamous cell carcinoma.

In some embodiments, a biological sample comprises tumor cells that are refractory or resistant to one or more PD-1 antagonists. In some embodiments, the tumor cells are refractory or resistant to one or more PD-1 antagonists while maintaining activity to the PD-1 (e.g., PD-1, PD-L1, or PD-L2) pathway.

In certain embodiments, a biological sample comprises tumor cells of a cancer where carcinoembryonic antigen related cell adhesion molecule 1 (CEACAM1) is expressed. In some embodiments, the biological sample comprises tumor cells, cancer stem cells, and/or tumor-infiltrating lymphocytes. For example, tumor cells include cells of a cancer such as carcinoma, lymphoma, blastoma, sarcoma, and leukemia. In some embodiments, a compound of Formula (I) modulates an immune response mediated by TIM-3 and CEACAM1, e.g., by decreasing T cell tolerance and treating cancer. In some embodiments, a biological sample comprises tumor cells of a lung cancer where CEACAM1 expression is associated with the consensus molecular subtype. In some embodiments, the biological sample comprises tumor cells of a squamous cell lung carcinoma. In some embodiments, the biological sample comprises tumor cells of a lung cancer of the secretory subtype. In some embodiments, a biological sample comprises tumor cells of a cancer where CEACAM1 is highly expressed. In some embodiments, the biological sample comprises tumor cells of a cancer selected from cancer of the adrenal gland, biliary tract cancer, renal cancer, liver cancer, pancreatic cancer, colon cancer, and rectal cancer. In some embodiments, the biological sample comprises tumor cells of a cancer selected from adrenocortical carcinoma, cholangiocarcinoma, kidney chromophobe, liver hepatocellular carcinoma, pancreatic adenocarcinoma, colon adenocarcinoma, and rectum adenocarcinoma.

In certain embodiments, a biological sample comprises tumor cells of a cancer where galectin-9 (Gal-9) is expressed. In some embodiments, the biological sample comprises tumor cells, cancer stem cells, and/or tumor-infiltrating lymphocytes. For example, tumor cells include cells of a cancer such as carcinoma, lymphoma, blastoma, sarcoma, and leukemia. In some embodiments, a compound of Formula (I) modulates an immune response mediated by TIM-3 and Gal-9, e.g., by decreasing T cell tolerance and treating cancer. In some embodiments, a biological sample comprises tumor cells of a lung cancer where Gal-9 expression is associated with the consensus molecular subtype. In some embodiments, the biological sample comprises tumor cells of a squamous cell lung carcinoma. In some embodiments, the biological sample comprises tumor cells of a lung cancer of the secretory subtype. In some embodiments, a biological sample comprises tumor cells of a cancer where Gal-9 is highly expressed. In some embodiments, the biological sample comprises tumor cells of a cancer selected from cancer of the adrenal gland, biliary tract cancer, renal cancer, liver cancer, pancreatic cancer, colon cancer, and rectal cancer. In some embodiments, the biological sample comprises tumor cells of a cancer selected from adrenocortical carcinoma, cholangiocarcinoma, kidney chromphobe, liver hepatocellular carcinoma, pancreatic adenocarcinoma, colon adenocarcinoma, and rectum adenocarcinoma.

In some embodiments, a biological sample comprises tumor cells of a cancer where TIM-3 is expressed. In some embodiments, the biological sample comprises tumor cells, $CD8^+$ T cells, and Tregs. For example, tumor cells include cells of a cancer such as Wilms tumor, prostate adenocarcinoma, colon carcinoma, melanoma, fibrosarcoma, and acute myelogenous leukemia (AML). In some embodiments, blockade of the PD-1 (e.g., PD-1, PD-L1, or PD-L2) pathway and inhibition of TIM-3 restores function to dysfunctional $CD8^+$ T cells (e.g., restoring tumor antigen-specific IFN-γ production) and deprograms potent intratumoral Tregs (e.g., drives the downmodulation of several genes associated with potent Treg-suppressor function) (A. C. Anderson, Cancer Immunol. Res., 2014, 2(5): 393-398).

In some embodiments, a biological sample comprises tumor cells of a cancer where TIM-3 is highly or moderately expressed. In some embodiments, the biological sample comprises tumor cells of a cancer selected from glioma, Hodgkin's lymphoma, non-Hodgkin's lymphoma, blastoma, renal cancer, breast cancer, lung cancer, testicular cancer, thymoma, acute myeloid leukemia, mesothelioma, and cancer of the head or neck. In some embodiments, the biological sample comprises tumor cells of a cancer selected from brain lower grade glioma, lymphoma, glioblastoma multiforme, kidney renal clear cell carcinoma, kidney renal papillary cell carcinoma, breast invasive carcinoma, lung adenocarcinoma, lung squamous cell carcinoma, testicular germ cell tumors, thymoma, acute myeloid leukemia, mesothelioma, and head and neck squamous cell carcinoma. In some embodiments, a biological sample comprises tumor cells of a lung cancer where TIM-3 expression is associated with the consensus molecular subtype. In some embodiments, the biological sample comprises tumor cells of a squamous cell lung carcinoma. In some embodiments, the biological sample comprises tumor cells of a lung cancer of a basal subtype or a secretory subtype. In some embodiments, the lung adenocarcinoma is a CMS6 molecular subtype (The Cancer Genome Atlas Research Network, Nature 2014, 511, 543-550).

In some embodiments, a biological sample comprises tumor cells of a cancer where TIM-3 is moderately or highly expressed. In some embodiments, the biological sample comprises tumor cells of a cancer selected from glioma, Hodgkin's lymphoma, non-Hodgkin's lymphoma, blastoma, renal cancer, breast cancer, lung cancer. In some embodiments, the biological sample comprises tumor cells of a cancer selected from brain lower grade glioma, lymphoma, glioblastoma multiforme, kidney renal clear cell carcinoma, kidney renal papillary cell carcinoma, breast invasive carcinoma, lung adenocarcinoma, and lung squamous cell carcinoma. In some embodiments, a biological sample comprises tumor cells of a cancer where TIM-3 expression was correlated with expression of a myeloid pathway, a mixed APC, and a T and NK cell signature. In some embodiments, the biological sample comprises tumor cells of a cancer selected from cancer of the bladder, breast cancer, colorectal cancer, rectal cancer, cancer of the head or neck, lung cancer, prostate cancer, melanoma, and stomach cancer. In some embodiments, the biological sample comprises tumor cells of a cancer selected from bladder urothelial carcinoma, breast invasive carcinoma, colon adenocarcinoma, rectum adenocarcinoma, head and neck squamous cell carcinoma, lung adenocarcinoma, lung squamous cell carcinoma, prostate adenocarcinoma, skin cutaneous melanoma, and stomach adenocarcinoma.

In some embodiments, a biological sample comprises tumor cells of a cancer where TIM-3 expression correlated with expression of a myeloid pathway. In some embodiments, the biological sample comprises tumor cells of a cancer selected from cancer of the bladder, breast cancer, colorectal cancer, rectal cancer, cancer of the head or neck, lung cancer, prostate cancer, melanoma, stomach cancer, cancer of the adrenal gland, glioma, cervical cancer, biliary tract cancer, cancer of the esophagus, blastoma, renal cancer, liver cancer, mesothelioma, ovarian cancer, pancreatic cancer, sarcoma, testicular cancer, thyroid cancer, and uterine cancer. In some embodiments, the biological sample comprises tumor cells of a cancer selected from bladder urothelial carcinoma, breast invasive carcinoma, colon adenocarcinoma, rectum adenocarcinoma, head and neck squamous cell carcinoma, lung adenocarcinoma, lung squamous cell carcinoma, prostate adenocarcinoma, skin cutaneous melanoma, stomach adenocarcinoma, adrenocortical carcinoma, brain lower grade glioma, cervical squamous cell carcinoma, endocervical adenocarcinoma, cholangiocarcinoma, esophageal cancer, glioblastoma multiforme, kidney chromophobe, hepatocellular cancer, lymphoid neoplasm diffuse large B-cell lymphoma, mesothelioma, ovarian serous cystadenocarcinoma, pancreatic adenocarcinoma, pheochromocytoma, paraganglioma, sarcoma, testicular germ cell tumor, thyroid carcinoma, uterine carcinosarcoma, uterine corpus endometrial carcinoma and uveal melanoma. In some embodiments, TIM-3 expression is associated with expression of a dendritic cell pathway or expression of a macrophage pathway. In some embodiments, a biological sample comprises tumor cells of a colorectal cancer where TIM-3 expression correlated with expression of a myeloid pathway. In some embodiments, the colorectal cancer is a consensus molecular subtype. In some embodiments, a biological sample comprises tumor cells of a cancer where TIM-3 expression correlated with expression of a T cell pathway. In some embodiments, the biological sample comprises tumor cells of a cancer selected from cancer of the adrenal gland, biliary tract cancer, renal cancer, glioma, testicular cancer, and thyroid cancer. In some embodiments, the biological sample comprises tumor cells of a cancer selected from adrenocortical carcinoma, cholangiocarcinoma, kidney chromophobe, brain lower grade glioma, pheochromocytoma, paraganglioma, testicular germ cell tumor, and thyroid carcinoma.

In some embodiments, a biological sample comprises tumor cells of a cancer where TIM-3 expression correlated with expression of an interferon gamma (IFN-gamma) pathway. In some embodiments, the biological sample comprises tumor cells of a cancer selected from glioma, testicular cancer, and thyroid cancer. In some embodiments, the biological sample comprises tumor cells of a cancer selected from brain lower grade glioma, testicular germ cell tumor, and thyroid carcinoma.

In some embodiments, the biological sample comprises tumor cells of a cancer selected from breast cancer, lung cancer, prostate cancer, colon cancer, and pancreatic cancer. In some embodiments, the biological sample comprises tumor cells of a cancer selected from breast adenocarcinoma, squamous and adenocarcinoma of the lung, prostate adenocarcinoma, colon adenocarcinoma and pancreatic adenocarcinoma.

In some embodiments, a biological sample comprises tumor cells of a cancer where TIM-3 expression correlated with mixed signatures associated with macrophages, mast cells, eosinophils, neutrophils, or dendritic cells. In some embodiments, the biological sample comprises tumor cells of a lung cancer. In some embodiments, the lung cancer is a lung adenocarcinoma. In some embodiments, a biological sample comprises tumor cells of a cancer where TIM-3 expression correlated with mixed signatures associated with T cells, mast cells, or neutrophils. In some embodiments, the biological sample comprises tumor cells of a breast cancer.

In some embodiments, a biological sample comprises tumor cells of a cancer where TIM-3 expression correlated with mixed lymphocyte pathways. In some embodiments, the biological sample comprises tumor cells of a pancreatic cancer.

In some embodiments, a biological sample comprises tumor cells of a cancer where CEACAM1 expression correlated with mixed lymphocyte pathways, including interferon gamma response genes. In some embodiments, the biological sample comprises tumor cells of a prostate cancer.

In some embodiments, a biological sample comprises tumor cells of a cancer where CEACAM1 expression correlated with increased expression of interferon response pathways, expression of a T cell pathway, or expression of a myeloid pathway. In some embodiments, the biological sample comprises tumor cells of a lung cancer. In some embodiments, the biological sample comprises tumor cells of a squamous cell lung carcinoma. In some embodiments, a biological sample comprises tumor cells of a cancer where CEACAM1 expression correlated with increased expression of interferon response pathways and expression of a T cell pathway. In some embodiments, the biological sample comprises tumor cells of a squamous cell lung adenocarcinoma.

In some embodiments, a biological sample comprises tumor cells of a cancer where CEACAM1 expression is correlated with a clinical variable selected from hormone receptor (HR) status, triple negative status, PAM50+ subtype (Parker, J. S., et al., *J. Clin. Oncol.*, 2009, 27(8): 1160-1167) and mutation count. In some embodiments, the biological sample comprises tumor cells of a breast cancer. In some embodiments, the biological sample comprises tumor cells of a breast cancer selected from triple negative breast cancer, estrogen receptor positive (ER+), progesterone receptor positive (PR+), and/or human epidermal growth factor receptor 2 (HER2+). In other embodiments, the biological sample comprises tumor cells of a PAM50+ breast cancer assay panel (Parker. J. S., et al., *J. Clin. Oncol.*, 2009, 27(8): 1160-1167), breast cancer selected from luminal A, luminal B, HER2-enriched, basal-like and normal-like. In some embodiments, the biological sample comprises tumor cells of a triple negative BRCA breast cancer and basal-like breast cancer.

In some embodiments, a biological sample comprises tumor cells of a cancer where TIM-3 expression is correlated with CEACAM1 expression. In some embodiments, TIM-3 and CEACAM1 expression is associated with GLEASON pattern primary, circulating nucleic acids, and disease-free survival. In some embodiments, the biological sample comprises tumor cells of a prostate cancer. In some embodiments, TIM-3 expression predicts overall survival in CEACAM1 intermediate expression individuals and CMS1 (ERG) samples. In some embodiments, TIM-3 expression predicts disease-free survival in CEACAM1 high expression individuals.

In some embodiments, a biological sample comprises tumor cells of a cancer where TIM-3 expression is correlated with low CEACAM1 expression and predicts overall survival. In some embodiments, the biological sample comprises tumor cells of a breast cancer.

In some embodiments, a biological sample comprises tumor cells of a cancer where CEACAM1 expression is correlated with low TIM-3 expression and predicts overall survival. In some embodiments, the biological sample comprises tumor cells of a breast cancer with overall survival.

In some embodiments, a biological sample comprises tumor cells of a cancer where expression of CEACAM1 predicts disease free survival. In some embodiments, the biological sample comprises tumor cells of a prostate cancer, a colorectal cancer, or a lung cancer. In some embodiments, the colorectal cancer is CMS2 (canonical) or CMS4 (mesenchymal) (Guinney et al Nature Med 2015, 21, 1350-1356). In some embodiments, the lung cancer is a lung adenocarcinoma.

In some embodiments, a biological sample comprises tumor cells of a cancer where expression of CEACAM1 predicts overall survival. In some embodiments, expression of CEACAM1 is high to moderate. In some embodiments, the biological sample comprises tumor cells of a lung cancer. In some embodiments, the lung cancer is a lung adenocarcinoma.

In some embodiments, a biological sample comprises tumor cells of a cancer where low expression of CEACAM1 predicts disease free survival. In some embodiments, the biological sample comprises tumor cells of a pancreatic cancer or a prostate cancer. In some embodiments, the biological sample comprises tumor cells of a prostate cancer with a CMS1 (Erg) phenotype.

In some embodiments, a biological sample comprises tumor cells of a cancer where TIM-3 expression predicts overall survival or disease free survival. In some embodiments, TIM-3 expression is correlated with overall survival. In some embodiments, TIM-3 expression is correlated with disease free survival. In some embodiments, the biological sample comprises tumor cells of a pancreatic cancer. In some embodiments, the biological sample comprises tumor cells of a pancreatic cancer with a CMS2 phenotype. In some embodiments, the biological sample comprises tumor cells of a lung cancer. In some embodiments, the lung cancer is a squamous cell lung carcinoma with an intermediate circulating nucleic acid load and/or in the secretory subtype. In some embodiments, the lung adenocarcinoma is a subtype selected from high TIM-3 expression, high CEACAM1 expression, and a CMS6 molecular subtype (The Cancer Genome Atlas Research Network, Nature 2014, 511, 543-550). In some embodiments, the lung adenocarcinoma has high TIM-3 expression.

Other embodiments of the present disclosure provide a method of treatment of infection by inhibition of TIM-3.

Still other embodiments of the present disclosure provide a method of treatment of infection by blockade of the PD-1 pathway and inhibition of TIM-3, for example inhibiting an immunosuppressive signal induced by PD-1, PD-L1, or PD-L2 and/or TIM-3, wherein the method comprises administration of a therapeutically effective amount of a compound of Formula (I) to the subject in need thereof.

In certain embodiments, the present disclosure provides uses of a compound of the present disclosure for the preparation of a medicament for the treatment of infectious disease, as well as methods of administering a therapeutically effective amount of a compound of Formula (I) for the treatment of infectious disease.

In some embodiments, the infectious disease is bacterial infection, viral infection, fungal infection, or parasitic infection, as well as methods of administering a therapeutically effective amount of a compound of Formula (I) for the treatment of bacterial infection, viral infection, fungal infection, or parasitic infection.

In some embodiments, for example, bacterial infection may be caused by at least one bacterium selected from anthrax, *Bacilli, Bordetella, Borrelia,* botulism, *Brucella, Burkholderia, Campylobacter, Chlamydia,* cholera, *Clostridium, Conococcus, Corynebacterium,* diptheria, *Enterobacter, Enterococcus, Erwinia, Escherichia, Francisella, Haemophilus, Heliobacter, Klebsiella, Legionella, Leptospira,* leptospirosis, *Listeria,* Lyme's disease, *meningococcus, Mycobacterium, Mycoplasma, Neisseria, Pasteurella, Pelobacter,* plague, *Pneumonococcus, Proteus, Pseudomonas, Rickettsia, Salmonella, Serratia, Shigella, Staphylococcus, Streptococcus,* tetanus, *Treponema, Vibrio, Yersinia* and *Xanthomonas*.

In other embodiments, for example, viral infection may be caused by at least one virus selected from Adenoviridae, Papillomaviridae, Polyomaviridae, Herpesviridae, Poxviridae, Hepadnaviridae, Parvoviridae, Astroviridae, Caliciviridae, Picornaviridae, Coronoviridae, Flaviviridae, Retroviridae, Togaviridae, Arenaviridae, Bunyaviridae, Filoviridae, Orthomyxoviridae, Paramyxoviridae, Rhabdoviridae, and Reoviridae. In certain embodiments, the virus may be arboviral encephalitis virus, adenovirus, herpes simplex type I, herpes simplex type 2, Varicella-zoster virus, Epstein-barr virus, cytomegalovirus, herpesvirus type 8, papillomavirus, BK virus, coronavirus, echovirus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus, orbivirus, coltivirus, vaccinia virus, and Banna virus.

In other embodiments, for example, fungal infection may be selected from thrush, *Aspergillus (fumigatus, niger,* etc.),

*Blastomyces dermatitidis, Candida (albicans, krusei, glabrata, tropicalis,* etc.), *Coccidioides immitis, Cryptococcus (neoformans,* etc.). *Histoplasma capsulatum, Mucorales (mucor, absidia, rhizophus), Paracoccidioides brasiliensis,* sporotrichosis, *Sporothrix schenkii,* zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, and rhinosporidiosis.

In some embodiments, for example, parasitic infection may be caused by at least one parasite selected from *Acanthamoeba, Babesia microti, Balantidium coli, Entamoeba hystolytica, Giardia lamblia, Cryptosporidium muris, Trypanosomatida gambiense, Trypanosomatida rhodesiense, Trypanosoma brucei, Trypanosoma cruzi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Pneumocystis carinii, Trichomonas vaginalis, Histomonas meleagridis, Secementea, Trichuris trichiura, Ascaris lumbricoides, Enterobius vermicularis, Ancylostoma duodenale, Naegleria fowleri, Necator americanus, Nippostrongylus brasiliensis, Strongyloides stercoralis, Wuchereria bancrofti, Dracunculus medinensis,* blood flukes, liver flukes, intestinal flukes, lung flukes, *Schistosoma mansoni, Schistosoma haematobium, Schistosoma japonicum, Fasciola hepatica, Fasciola gigantica, Heterophyes heterophyes,* and *Paragonimus westermani.*

Other embodiments of the present disclosure provide a method of treatment of an autoimmune or an inflammatory disease by inhibition of TIM-3.

Still other embodiments of the present disclosure provide a method of treatment of an autoimmune or an inflammatory disease by blockade of the PD-1 pathway and inhibition of TIM-3, for example inhibiting an immunosuppressive signal induced by PD-1, PD-L1, or PD-L2 and/or TIM-3, wherein the method comprises administration of a therapeutically effective amount of a compound of Formula (I) to the subject in need thereof.

In certain embodiments, the present disclosure provides uses of a compound of the present disclosure for the preparation of a medicament for the treatment of an autoimmune or an inflammatory disease, as well as methods of administering a therapeutically effective amount of a compound of Formula (I) for the treatment of an autoimmune or an inflammatory disease.

In some embodiments, the autoimmune or inflammatory disease is selected from intestinal mucosal inflammation, wasting disease associated with colitis, multiple sclerosis, systemic lupus erythematosus, rheumatoid arthritis, type I diabetes, osteoarthritis, psoriasis, Crohn's disease, atherosclerosis, allergic conditions (e.g., allergic encephalomyelitis, asthma), and glomerulonephritis, and inflammatory bowel disease. In some embodiments, the autoimmune or inflammatory disease is selected from multiple sclerosis, rheumatoid arthritis, type I diabetes. Crohn's disease, atherosclerosis, allergic conditions (e.g., allergic encephalomyelitis, asthma), and glomerulonephritis.

Biomarker Screening

Gene expression profiles of a tissue of interest, such as a tumor tissue, can be obtained and therapeutic treatments can be selected based on the gene expression profile. In other words, if an anti-tumor agent acts by inhibiting a particular oncoprotein, it may be desirable to know whether a particular cancer expresses that oncogene before attempting to treat the cancer with the anti-tumor agent. The expression of a particular gene can be assessed in many ways. The level of gene transcript or the level of encoded protein may be determined. The presence of a protein may be determined directly, through methods such as antibody binding, mass spectroscopy and two-dimensional gel electrophoresis, or indirectly, by detecting an activity of the protein, be it a biochemical activity or an effect on the levels of another protein or expression of one or more genes.

A number of methodologies are currently used for the measurement of gene expression. In some embodiments, these methodologies utilize the polymerase chain reaction (PCR) technique, the details of which are provided in U.S. Pat. No. 4,683,195, 4,683,202, and 4,965,188, all to Mullis et al., all of which are specifically incorporated herein by reference in its entirety. In other embodiments. methodologies utilize digital detection of a transcript by a probe hybridized to a segment of DNA that is attached to a unique string of colored fluorophones (also referred to as the molecular barcode).

In addition, certain methodologies also include the analysis of the mutational burden of the tumor.

Methodologies also include comparative genomic hybridization (CGH); fluorescence in situ hybridization (FISH); immunohistochemistry (IHC); and next-generation sequencing (NGS), and other molecular profiling techniques assessing DNA levels (e.g., genomic arrays), RNA quantification, proteomic assays, other technologies that allow the multiplex analysis of gene expression profiles, and the like.

As used herein, a "signature" is a pattern of expression of a defined subset of genes or biomarkers.

As used herein, a "highly immune signature positive" sample represents immune cell tumor infiltration by specific types of immune cells, such as but not limited to cytotoxic T cells.

For example, in certain methods of treating cancer disclosed herein, the method may comprise determining whether a biological sample comprising tumor cells express (or overexpress, relative to normal tissue of that tissue type) a biomarker such as galectin-9, $CD11b^+Gr-1^+$, carcinoembryonic antigen related cell adhesion molecule 1 (CEACAM1), high-mobility group box 1 (HMGB1), phosphatidyl serine, and leukocyte immunoglobulin-like receptor A3 (LILRA3), TIM-3, PD-L1, or PD-L2. Similarly, the methods may comprise determining whether the biological sample is TIM-3 positive, myeloid signature positive, natural killer signature positive, and/or immune signature positive. A patient's tumor may be biopsied to obtain a sample for testing, although the sample may be obtained in any other suitable way, such as by identifying shed or metastatic tumor cells or nucleic acid in the subject's bloodstream. In some embodiments, the sample may be tested in situ in the patient. Alternatively, the sample may be a blood sample, and determining whether the tumor overexpresses a marker may comprises measuring the level of the marker in the blood sample to determine whether the level is indicative of normal expression of the marker or of elevated expression of the marker.

In some embodiments, a biological sample may exhibit elevated expression of TIM-3 and other markers of activation of the immune system. For example, a biological sample may exhibit a certain signature, e.g., be immune signature positive. In other embodiments, a patient who exhibits a particular gene signature may then be treated with a compound of Formula (I). In some embodiments, TIM-3 exhibits elevated expression on tumor cells, cancer stem cells, or $CD8^+$ T cells, and Tregs. For example, TIM-3 is specifically expressed on leukemic stem cells (LSC) but not on normal hematopoietic stem cells (HSC) in AML.

In some embodiments, a patient who exhibits elevated expression, e.g., of galectin-9, CD11b⁺Gr-1⁺, CEACAM1, HMGB1, LILRA3, LILRB2, phosphatidyl serine, TIM-3, PD-L1, and/or PD-L2, may then be treated with a compound as disclosed herein. In some embodiments, the expression of TIM-3 and interaction with a TIM-3 agent promotes certain cell populations. For example, the expression of TIM-3 and interaction with galectin-9 promotes CD11b⁺Gr-1⁺ myeloid-derived suppressor cells (MDSC). In another example, the expression of TIM-3 and interaction with HMGB1 on tumor-associated dendritic cells (TADC) interferes with sensing of DNA released by cells undergoing necrotic cell death. That is, interaction of TIM-3 with HMGB1 can dampen immune activation (e.g., chemotherapy approaches that trigger immunogenic cell death). In another example the expression of TIM-3 and interaction with leukocyte immunoglobulin-like receptor A3 (LILRA3) can stimulate the secretion of myeloid-associated cytokines (IL-12, TNF-α, IL-Iβ, GM-CSF or IL-6). In some embodiments, elevated expression of CEACAM1 on tumor cells correlates with poor prognosis and a high risk of metastasis.

Accordingly, provided herein are methods of modulating an immune response in a subject, comprising
a) determining whether a biological sample from a subject overexpresses galectin-9, CD11b⁺Gr-1⁺, CEACAM1, HMGB1, phosphatidyl serine, TIM-3, PD-L1, and/or PD-L2; and
b) contacting the subject with a compound of Formula (I) as disclosed herein if the sample overexpresses galectin-9, CD11b⁺Gr-1⁺, CEACAM1, HMGB1, phosphatidyl serine, TIM-3, PD-L1, and/or PD-L2.

In some embodiments, provided herein are methods of modulating an immune response in a subject, comprising
a) determining whether a biological sample from a subject overexpresses TIM-3; and
b) contacting the subject with a compound of Formula (I) as disclosed herein if the sample overexpresses TIM-3.

In some embodiments, provided herein are methods of modulating an immune signature in a subject, comprising
a) determining whether a biological sample from a subject overexpresses TIM-3; and
b) contacting the subject with a compound of Formula (I) as disclosed herein if the sample overexpresses TIM-3.

In some embodiments, the method further comprises determining whether the sample also overexpresses galectin-9, CD11b⁺Gr-1⁺, CEACAM1, HMGB1, phosphatidyl serine, PD-L1 or PD-L2. In other embodiments, the methods disclosed herein further comprise determining whether the sample also overexpresses a marker of activation of the immune system. In certain embodiments, the sample comprises one or more tumor cells.

Another application of assessing gene expression is in the development of companion diagnostic (CDx) tools for determining whether a drug or other therapeutic agent will be beneficial to the subject having a disease or condition modulated by that gene's activity. A CDx can guide the use of a drug to only patients having the gene, gene signature, or protein affected by the therapy and can be a required element in an FDA approved therapy. Subjects benefit from not being prescribed drugs that will not have a beneficial effect for a disease, e.g. a certain cancer, and allow the physician to tailor therapy on a patient by patient basis. Thus, it is paramount that the CDx be analytically and clinically validated to minimize any false positive or negative effects. For this reason, CDx tests are often developed in parallel with the drug development. An effective CDx must have a high and reproducible correlation with the disease or condition being assessed.

In certain embodiments, provided herein is a method of identifying the likelihood of modulating an immune response in a subject with a compound of Formula (I), the method comprising:
a) obtaining or providing a biological sample from a subject;
b) measuring the amount or activity of TIM-3 in the subject sample; and
c) comparing the measured amount or activity to an amount or activity of the TIM-3 in a control sample,
wherein a significantly increased amount or activity of TIM-3 in the subject sample relative to the control sample identifies the subject as being more likely to be responsive to the compound of Formula (I), and wherein a similar or decreased amount or activity of TIM-3 in the subject sample relative to the control sample identifies the subject as being less likely to be responsive to the compound of Formula (I), In other embodiments, provided herein is a method of identifying the likelihood of modulating an immune response in a subject with a compound of Formula (I), the method comprising:
a) obtaining or providing a biological sample from a subject;
b) measuring the amount or activity of TIM-3 in the subject sample; and
c) comparing the measured amount or activity to an amount or activity of the TIM-3 in a control sample,
wherein a similar or decreased activity of TIM-3 in the subject sample relative to the control sample identifies the subject as being more likely to be responsive to the compound of Formula (I), and
wherein a high amount or activity of TIM-3 in the subject sample relative to the control sample identifies the subject as being less likely to be responsive to the compound of Formula (I).

In certain embodiments, the biological sample is selected from serum, whole blood, plasma, urine, cells (e.g., tumor cells), cell lines, surgically recessed tumor tissue, and tissue biopsies. In some embodiments, the sample is selected from whole blood or a tissue biopsy. In certain embodiments, the sample comprises biomarkers, e.g., galectin-9, CEACAM1, HMGB1, phosphatidyl serine, TIM-3, PD-L1, and/or PD-L2, from the subject. In other embodiments, the subject exhibits a particular gene signature as the biomarker. In other embodiments, the gene signature includes TIM-3 expression. In some embodiments, the subject has cancer as described herein. In some embodiments, the method further comprises recommending, prescribing, or administering a compound of Formula (I) if the subject is determined likely to be responsive to a compound of Formula (1) or administering a therapy other than a compound of Formula (I) if the subject is determined be less likely to be responsive to a compound of Formula (I).

In certain embodiments, the control sample is a sample from either the subject or a member of the same species to which the patient belongs, or even a healthy tissue sample obtained from the same subject. The control sample may comprise cells or not comprise cells. The control sample may comprise cancer cells known to be responsive or non-responsive to a compound of Formula (I).

In certain embodiments, the amount of TIM-3 is detected using a reagent which specifically binds with the protein. In certain embodiments, the reagent is selected from an antibody, an antibody derivative, and an antibody fragment. In certain embodiments, TIM-3 expression is assessed by detecting the presence in the sample of a transcribed polynucleotide or portion thereof. In certain embodiments, the transcribed polynucleotide is an mRNA or a cDNA. In certain embodiments, detecting further comprises amplifying the transcribed polynucleotide. In certain embodiments, the transcribed polynucleotide is detected by identifying a nucleic acid that anneals with the biomarker nucleic acid, or a portion thereof, under stringent hybridization conditions. In other embodiments, the detection of a gene signature as a biomarker may be based on methods including, but not limited to, next-generation sequencing (NGS), hybridization, and digital detection. For example, multiplex sequencing is an NGS method that uses parallel sequencing and unique index tags allowing pooled samples to be analyzed simultaneously. Digital detection relies on discrete units for measurement rather than relying on relative levels of signals. For example, a transcript is detected by a probe hybridized to a segment of DNA that is attached to a unique string of colored fluorophores (molecular barcode), and the total number of transcripts in the sample is quantified by counting the number of times a particular molecular barcode is detected.

The expression of TIM-3 in a subject is "significantly" higher or lower than the normal amount of the biomarker, if the amount of TIM-3 is greater or less, respectively, than the normal level by an amount greater than the standard error of the assay employed to assess amount, and preferably at least about 0.2×, 0.3×, 0.4×, 0.5×, 0.6×, 0.7×, 0.8×, 0.9×, 1×, 1.5×, 2×, 2.5×, 3×, 3.5×, 4×, 5×, 6×, 7×, 8×, 9×, or 10× than that amount. Alternatively, the amount of TIM-3 in the subject can be considered "significantly" higher or lower than the normal amount if the amount is at least about two, and preferably at least about three, four, or five times, higher or lower, respectively, than the normal amount of TIM-3. Such "significance" can also be applied to any measured parameter described herein, such as for expression, inhibition, cytotoxicity, cell growth, and the like.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody.

The term "control" refers to any reference standard suitable to provide a comparison to the expression products in the test sample. In certain embodiments, the control comprises obtaining a "control sample" from which expression product levels are detected and compared to the expression product levels from the test sample. Such a control sample may comprise any suitable sample, including but not limited to a sample from a control subject (can be stored sample or previous sample measurement) with a known outcome; normal tissue or cells isolated from a subject, cultured primary cells/tissues isolated from a subject, adjacent normal cells/tissues obtained from the same organ or body location of the subject, a tissue or cell sample isolated from a normal subject, or a primary cells/tissues obtained from a depository. In certain embodiments, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome or receiving a certain treatment. It will be understood by those of skill in the art that such control samples and reference standard expression product levels can be used in combination as controls in the methods of the present invention.

The "normal" level of expression of TIM-3 is the level of expression of TIM-3 in cells of a subject, e.g., a human patient, not in need of immune response modulation. An "over-expression" or "significantly higher level of expression" of a biomarker refers to an expression level in a test sample that is greater than the standard error of the assay employed to assess expression, and is preferably at least about 10%, and more preferably about 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of TIM-3 in a control sample (e.g., sample from a healthy subject not in need of immune modulation, or from a healthy tissue sample obtained from the same subject) and preferably, the average expression level of the biomarker in several control samples. A "significantly lower level of expression" of a biomarker refers to an expression level in a test sample that is at least about 10%, and more preferably about 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not in need of immune modulation) and preferably, the average expression level of the biomarker in several control samples.

The term "sample" used for detecting or determining the presence or level of the TIM-3 gene is typically whole blood, plasma, scrum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In some embodiments, the disclosed methods further comprise obtaining the sample from the subject prior to detecting or determining the presence or level of the TIM-3 gene.

Methods of Administration

The compounds of the present disclosure may be used as single drugs (monotherapy) or conjointly with one or more other agents (conjoint therapy). The compounds may be used by themselves, or, preferably, in a pharmaceutical composition in which the compound is mixed with one or more pharmaceutically acceptable materials.

The pharmaceutical composition may be administered by oral or inhalation routes, or by parenteral administration route. For example, compositions can be administered orally, by intravenous infusion, topically, intraperitoneally, intravesically, intrathecally, or as a suppository. Examples of parenteral administration includes but not limited to intraarticular (in the joints), intravenous, intramuscular, intradermal, intraperitoneal, and subcutaneous routes. Suitable liquid compositions may be aqueous or non-aqueous, isotonic sterile injection solutions, and may contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Oral administration, parenteral administration, subcutaneous administration and intravenous administration are preferred methods of administration.

The dosage of the compounds of the present disclosure varies depending on a patient's age, weight, or symptoms, as well as the compound's potency or therapeutic efficacy, the dosing regimen and/or treatment time. Generally, suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections. The compounds of the disclosure may be administered in an amount of 0.5 mg or 1 mg up to 500 mg, 1 g, or 2 g per dosage regimen. The dosage may be administered once per week, once per three days, once per two days, once per day, twice per day, three times per day, or more often. In alternative embodiments, in certain adults the compound can be continuously administered by intravenous administration for a period of time designated by a physician. Since the dosage is affected by various conditions, an amount less than or greater than the dosage ranges contemplated about may be implemented in certain cases. A physician can readily determine the appropriate dosage for a patient undergoing therapeutic treatment.

Combination Therapy

The compounds of the present disclosure may be administered in combination with one or more other drugs (1) to complement and/or enhance effect of the compound of Formula (I). (2) to modulate pharmacodynamics, improve absorption, or reduce dosage of the compound of Formula (I), and/or (3) to reduce or ameliorate the side effects of the compound Formula (I). As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds. The respective compounds may be administered by the same or different route and the same or different method. In some embodiments, the combined effect of conjoint therapy is detectable through immune effects.

The dosage of the other drug can be a dosage that has been clinically used, or may be an altered dosage such that the dosage is effective when administered in combination with a compound of the present disclosure. The ratio of the compound of the present disclosure and the other drug can vary according to age and weight of a subject to be administered, administration method, administration time, disorder to be treated, symptom and combination thereof. For example, the other drug may be used in an amount of 0.01 to 100 parts by mass, based on 1 part by mass of the compound of the present disclosure.

Conjoint therapy can be employed to treat any diseases discussed herein. In certain embodiments, a compound of Formula (I) of the disclosure may be conjointly administered with another therapeutic agent, e.g., an anti-cancer agent, an anti-viral agent, a cytokine or an immune agonist. In some embodiments, the other therapeutic agent is selected from CTLA-4 antagonists, PD-1 antagonists, PD-L1 antagonists, or PD-L2 antagonists, and EGFR antagonists.

Agents for Combination Therapies

In certain embodiments, a compound of Formula (I) can be conjointly administered with another therapeutic agent, e.g., 1) an aldosterone synthase inhibitor;
2) an ALK inhibitor; an apoptosis inducer;
3) an aromatase inhibitor;
4) a CART cell (e.g., a CART cell targeting CD19);
5) a BCR-ABL inhibitor;
6) a BRAF inhibitor;
7) a CDK4/6-inhibitor;
8) a CEACAM (e.g., CEACAM-1, -3 and/or -5) inhibitor;
9) a c-KIT inhibitor;
10) a c-MET inhibitor;
10) a cRAP inhibitor;
11) a CTLA4 inhibitor,
12) a cytochrome P450 inhibitor (e.g., a CYP17 inhibitor);
13) an EGF inhibitor;
14) an ERK1/2 ATP inhibitor;
15) an FGF inhibitor (e.g., a FGFR2 or FGFR4 inhibitor);
16) a Flt3 inhibitor (e.g., FLK2/STK1);
17) a P-Glycoprotein 1 inhibitor;
18) a HDAC inhibitor;
19) a HDM2 inhibitor;
20) a HER3 inhibitor;
21) a histamine release inhibitor;
22) an HSP90 inhibitor;
23) an IAP inhibitor,
24) an IDH inhibitor;
25) an IDO inhibitor
26) an IGF-1R inhibitor;
27) an iron chelating agent;
28) a Janus inhibitor,
29) a LAG-3 inhibitor;
30) an M-CSF inhibitor;
31) a MEK inhibitor;
32) an mTOR inhibitor;
33) a p53 inhibitor (e.g., an inhibitor of a p53/Mdm2 interaction);
34) a PDGFRβ inhibitor;
35) a PKC inhibitor;
36) a PI3K inhibitor;
37) a PIM inhibitor;
38) a PRLR inhibitor;
39) a Raf kinase C inhibitor,
40) a smoothened (SMO) receptor inhibitor;
41) a somatostatin agonist and/or a growth hormone release inhibitor;
42) a transduction modulator and/or angiogenesis inhibitor;
43) a VEGFR-2 inhibitor (e.g., FLK-1/KDR);
44) a tyrosine kinase inhibitor (e.g., CSF-1R tyrosine kinase);
45) a Wnt signaling inhibitor;
46) a Bcl-2 inhibitor;
47) a Mcl-1 inhibitor;
48) a BTK inhibitor;

49) dual active molecules such as CUDC-907 (a dual PI3K/HDAC inhibitor);
50) a BET bromodomain inhibitor;
51) an Arginase-1 inhibitor; and
52) a PD-1 inhibitor.

Additional therapeutic agents suitable for conjoint administration with the compounds and compositions disclosed herein have been described, for example, in the following publications: WO2016/100882; WO2016/054555; WO2016/040892; WO2015/097536; WO2015/088847; WO2015/069770; WO2015/026634; WO 2015/009856; EP 1377609 B1; Antonia, et al. Clin. Cancer Res. 2014 20: 6258-6268; and Melero, et al. Nature Reviews Cancer 2015 15: 457-472. Each publication is incorporated herein by reference in its entirety.

For example, in the methods of the disclosure directed to the treatment of cancer, the compound of the present disclosure can be used with another chemotherapeutic conjointly as a single pharmaceutical composition or a combination of different pharmaceutical compositions. Non-limiting examples of the chemotherapeutic agent include an alkylation agent, nitrosourea agent, antimetabolites, anticancer antibiotics, vegetable-origin alkaloids, topoisomerase inhibitors, hormone drugs, hormone antagonists, leucopenia (neutropenia) treatment drugs, thrombocytopenia treatment drugs, antiemetics, aromatase inhibitors, P-glycoprotein inhibitors, platinum complex derivatives, other immunotherapeutic drugs and other anticancer drugs.

Exemplary cytotoxic agents that can be administered conjointly include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation). For example, the cytotoxic agent can induce immunological cell death.

Non-limiting examples of additional therapeutic agents include, but are not limited to, peptides, polypeptides, proteins, fusion proteins, nucleic acid molecules, small molecules, mimetic agents, synthetic drugs, inorganic molecules, and organic molecules.

The pharmaceutical composition can contain, or the conjoint therapy can include, other compatible agents, e.g., a chemotherapeutic agent, a cytokine therapy, an interferon therapy (e.g., interferon-α, β, or γ; interferon α-2a; interferon α-2b; interferon α-m; interferon α-n3; interferon β-Ia; and interferon β-Ib), an interlukin therapy (e.g., IL-1, IL-2, IL-2Rβ, IL-2Rγ, IL-3, IL-7, IL7Rα, IL-11, IL-12, IL-15, and IL-21), a cluster of differentiation (CD) protein (e.g., CD2, CD4, CD7, CD8α, CD8β, CD11a/CD18, CD11b, CD11c, CD11d, CD18, CD19, CD19a, CD20, CD27, CD28, CD29, CD30, CD40, CD40L, CD49a, CD49D, CD49f, CD69, CD84, CD96, CD100, CD103, CD137, CD160, CD226, CD229, CD278) a co-stimulatory modulator, e.g., an agonist (e.g., an agonistic antibody or antigen-binding fragment thereof, or soluble fusion) of an MHC class I molecule, a TNF receptor protein, an immunoglobulin-like protein, a Toll ligand receptor, a NOD stimulant (e.g., mifurmatide), a CD83 ligand, a cytokine receptor, an integrin, signaling lymphocytic activation molecules (SLAM proteins), an activating NK cell receptor, an antibody therapy, a viral therapy, gene therapy or a combination thereof.

Chemotherapeutic and other therapeutic agents that may be conjointly administered with compounds of the disclosure include, but are not limited to: abiraterone, abraxane, aceglatone, acivicin, aclacinomysin, actimid, actinomycin, aflibercept, aldesleukin, aldophosphamide glycoside alectinib, alendronate, alitretinoin, altretamine, aminoglutethimide, aminolevulinic acid, aminopterin, amsacrine, anastrozole, ancitabine, angiostatin, angiozyme, anguidine, ansamitocin, anthramycin, antithrombin III, apatinib, arabinoside, arboplatin, asparaginase, authramycin, axitinib, azacitidine, azaserine, azetepa, azotomycin, 6-azauridine, baricitinib, batimastat, bendamustine, benimetinib, benzodopa, bestrabucil, bexarotene, bicalutamide, bisantrene, bleomycin, bortezomib, bosutinib, brequinar, brivanib, bryostatin, bropirimine, bullatacin, bullatacinone, buserelin, busulfan, cactinomycin, calichcamicin, callystatin, calusterone, caminomycin, campothecin, capecitabine, carabicin, carboplatin, carboquone, carfilzomib, carmofur, carmustine, carubicin, carzelesin, carzinophilin, cedefingol, cediranib, chlomaphazine, chlorambucil, chloroquine, chlorozotocin, cholophosphamide, chromomycin, cirolemycin, cisplatin, cisdichlorodiamine platinum (II), cisplatin, cladribine, clodronate, cobimetinib, colchicine, crisnatol, crizotinib, cryptophycin 1, cryptophycin 8, cyclophosphamide, cyproterone, cytarabine, cytochalasin B, cytosine arabinoside, dabrafenib, dacarbazine, dactinomycin, danoprevir, dasatinib, diaziquone, dibromomannitol, daunorubicin, decitabine, defofamine, degarelix, 1-dehydrotestosterone, delanzomib, demecolcine, demethoxyviridin, denileukin, denenicokin, denopterin, desacetylravidomycin, detorubicin, dexamethasone, dexormaplatin, dezaguanine, diaziquone, 6-diazo-5-oxo-L-norleucine, dichloroacetate, dideoxyuridine, dienestrol, diethylstilbestrol, diftitox, difluoromethylomithine, dihydroxyanthracindione, dinaciclib, docetaxel, dolastatin, dovitinib, doxifluridine, doxorubicin, doxycycline, droloxifene, dromostanolone, duazomycin, duocarmycin, dynemicin, edatrexate, eflomithine, elliptinium acetate, eleutherobin, emetine, emsirolimus, encorafenib, enloplatin, enocitabine, enpromate, epipropidine, epirubicin, epithilone, epitiostanol, erbulozole, erismodegib, erlotinib, esorubicin, esperamicin, estradiol, estramustine, etanidazole, ethidium bromide, 2-ethylhydrazide, etidronate, etoglucid, etoposide, everolimus, exemestane, fadrozole, fazarabine, fenretinide, filgrastim, floxuridine, fludarabine, fludrocortisone, fluorouracil, fluoxymesterone, flurocitabine, flutamide, foretinib, formestane, fosquidone, fotemustine, frolinic acid, gacytosine, gallium nitrate, galunisertib, gandotinib, gefitinib, geldanamycin, gemcitabine, genistein, glucocorticoids, goserelin, gramicidin D, herbimycin, hiltonol, 4-hydroxytamoxifen, hydroxyurea, ibandronate, idarubicin, ifosfamide, ilmofosine, imatinib, imiquimod, improsulfan, indoximod, interferon, iproplatin, irinotecan, ironotecan, ixazomib, keoxifene, laherparepvec, lameotide, lapatinib, lenalidomide, lestaurtinib, letrozole, leucovorin, leuprolide, lentinan, levamisole, liarozole, lidocaine, linifanib, lometrexo, lomustine, lonidamine, losoxantrone, marcellomycin, marizomib, masitinib, masoprocol, maytansyne, maytansinol, mechlorethamine, mechlorethamine oxide hydrochloride, mannomustine, medroxyprogesterone, megestrol, melengestrol, menogaril, melphalan, mepitiostane, mercaptopurine, mesna, metformin, methotrexate, metoprine, meturedopa, mithramycin, mitobronitol, mitoguazone, mitolactol, mitomycin, mitosper, mitotane, mitoxantrone, momelotinib, montanide, mopidamol, motesanib, motolimod, mycophenolic acid, mylotarg, nab-paclitaxel, navelbine, neratinib, nilotinib, nilutamide, nimustine, nitracrine, nocodazole, nogalamycin, novantrone, novembichin, obinutuzumab, octreotide, olivomycin, onapristone, ormaplatin, oxaliplatin, paclitaxel, pacritinib, palbociclib, pamidronate, pancratistatin, panobinostat, pazopanib, pegaptanib, pegaspargase, pegfilgrastim, peginterferon α-2b, pelitinib, pemetrexed, pentostatin, N4-pentoxycarbonyl-5-deoxy-5-fluorocytidine, peplomycin, perifosine, phenamet, phenesterine, pimasertib, pipobroman, piposulfan, pirarubicin, plicamycin, podophyllinic acid, polifeprosan, pomalidomide, porfimer, porfromycin, potfiromycin, prednimustine, procaine, procarbazine, propranolol, pteropterin, puromycin, quelamycin, raltitrexed, raloxifene, ranimustine, rapamycin, ravidomycin, razoxane, regorafenib, risedronate, resiquimod, rituximab, rodorubicin, rogletimide, roridin, ruxolitinib, safingol, sarcodictyin, selumetinib, semaxanib, semustine, simapimod, simtrazene, sirolimus, sizofiran, sorafenib, sparfosate, sparsomycin, spirogermanium, spiromustine, spiroplatin, spongistatin, streptonigrin, streptozocin, sulofenur, sunitinib, suramin, talisomycin, tamoxifen, talimogene, tasocitinib, taxol, tegafur, telatinib, teloxantrone, temoporfin, temozolomide, temsirolimus, teniposide, tenuazonic acid, teroxirone, testolactone, testosterone, tetracaine, tezacitibine, thalidomide, thiamiprine, thioguanine, thiotepa, tiazofurin, tiludronate, tirapazamine, titanocene, tivozanib, toceranib, tofacitinib, topoisomerase inhibitor RFS 2000, topotecan, toremifene, tozasertib, trametinib, trastuzumab, triaziquone, tretinoin, 2,2',2''-trichlorotriethylamine, triethylenemelamine, triethylenephosphoramide, triethylenethiophosphaoramide, trilostane, trimethylolomelamine, trimetrexate, triptorelin, trofosfamide, tubercidin, tuvizanib, uracil mustard, ubenimex, uredopa, urethane, vandetanib, vapreotide, vargatef, vatalanib, vemurafenib, verracurin, verteporfin, vinblastine, vincristine, vindesine, vinepidine, vinglycinate, vinleurosine, vinorelbine, vinrosidine, vinzolidine, vorozole, vismodegib, xeloda, zactima, zeniplatin, zinostatin, Ziv-aflibercept, zoledronate, and zorubicin.

In certain embodiments, exemplary chemotherapeutic agents include, but are not limited to, cytokines such as ABT-869, ACP-196, ADXS11-001, ADXS31-142, AEE788, AG-490, AM0010, AMN-107, AMP-224, AMP-514, AP24534, ARRY-142886, AST-6, AZD1480, AZD4547, AZD6094, AZD6244, AZD8055, AZD9291, B7-H3, BAFFR, 4-1BB, BEZ235, BGT 226, BHG712, BIBF 1120, BIBW2992, BIX 02188, BJG398, BKM-120, BMS-599626, BMS-690154, BMS-777607, BMS-911543, BMS-936558, BMS-936559, BMS-986016, BRAF-V600E, BTLA, BUW078, BYL719, CAL-101, CAL-263, CBI-TMI, CC-1065, CC-4047, CC-5013, CDS, CDX-1127, CEACAM1, CEP-701, CEP-11981, CGM097, Chi Lob 7/4, CI-1040, CO-1686, CP-673451, CP-870,893, CpG 7909, CPT-11, CRTAM, CT-011, CTL019, CTLA-4, CUDC-101, CYC116, CYT 387, DCC-2036, DNAM1, E6201, E7080, EGF816, FOLFOX6, G02443714, G-38963, GADS, GC1008, G-CSF, GDC-0032, GDC-0973, GDC-0980, GITR, GM-CSF, GR-MD-02, GSK1059615, GVAX, HVEM (LIGHTR), IA4, ICAM-1, ICOS, IMC-TR1, IMP321, INC280, INC424, INCB18424, INCB024360, INCB028050, IPH$_{2012}$, IPI926, IRX-2, ISA 51VG, ITGA4, ITGA6, ITGAD, ITGAE, ITGAL, ITGAM, ITGAX, ITGB1, ITGB2, ITGB7, JNJ-26483327, Ki8751, KIRDS2, KU-0063794, KW-289LAT, LBH$_{589}$, LCL161, LGH$_{447}$, LTBR, LDK378, LEE011, LGX818, LIGHT, LJM716, LY117018, LY2157299, LY294002, LY2940680, M-CSF, MARTI, MDX-1105, MDX-1106, MEDI0562, MEDI4736, MEDI4737, MEDI6383, MEDI6469, MEK162, MG-132, MGCD265, MK-3475, MK-4166, MM-121, MOXR0916, MP470, MPDL3280A, MSB-0010718C, NKG2C, NKG2D, NKp30, NKp44, NKp46, NKp80 (KLRF1), NY-ESO-1, ODC-0879, ODC-0980, ONX-0912, ODC-0941, OSI-027, OSI-930, OSK-1120212, OSK 2118436, OSK 2126458, OX40, P529, PAG/Cbp, PD153035, PD173074, PD0325901, PF-299804, PF-02341066, PF-04217903, PF-046915032, PF-05082566, PD98059, Poly(I:C), PKI-587, PLX4032, PLX4720, PSGL1, PSK, PX-886, Rad-001, RAF265, rHIgM12B7, R07204, RO4987655, RO6895882, RO7009789, SAR 245408, SAR 245409, SB-1317, SB-1518, SB-1578, SELPLG, SF1126, SGX523, SLAM, SLAMF4, SLAMF6, SLAMF7, SLAML_BLAME, SLP-76, SU 5402, T2 toxin, TEW 7197, TGN1412, TNFR2, TRANCE/RANKL, TriMix-DC, TRP-2, TRX518, TSU-68, VLA1, VLA-6, WYE-354, WZ3146, WZ4002, WZ8040, XL-147, XL-184, XL-228, XL-281, XL-647, XL-756, XL-765, XL-880, Yttrium90/MX-DTPA, and YW243.55.S70.

Exemplary paclitaxel agents that can be used conjointly with compounds disclosed herein include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG 105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87: 225-230), and glucose-conjugated paclitaxel (e.g., 2'paclitaxel methyl 2-glucopyranosyl succinate, see Liu et al., Bioorganic & Medicinal Chemistry Letters (2007) 17: 617-620).

In certain embodiments, exemplary chemotherapeutic agents include, but are not limited to:
1) (S)-N-((S)-1-cyclohexyl-2-((S)-2-(4-(4-fluorobenzoyl) thiazol-2-yl)pyrrolidin-1-yl)-2-oxoethyl)-2-(methylamino) propanamide;
2) ((1R, 9S,12S, 15R, 16E, 18R, 19R, 21R, 23S, 24E, 26E, 28E, 30S, 32S, 35R)-1,18-dihydroxy-12-{(IR)-2-[(1S, 3R,4R)-4-(2-hydroxyethoxy)-3-methoxycyclohexyl]-1-methylethyl}-19,30-dimethoxy-15,17,21,23,29,35-hexamethyl-11,36-dioxa-4-azatricyclo [30.3.1.04,9]hexatriaconta-16,24,26,28-tetraene-2,3,10,14,20-pentaone);
3) (S)-1-(4-chlorophenyl)-7-isopropoxy-6-methoxy-2-(4-{ methyl-[4-(4-methyl-3-oxopiperazin-1-yl)-trans-cyclohexylmethyl]-amino }phenyl)-1,4-dihydro-2H-isoquinolin-3one;
4) N-(4-((1R,3S,5S)-3-amino-5-methylcyclohexyl)pyridin-3-yl)-6-(2,6-difluoro phenyl)-5-fluoropicolinamide;
5) anti-HER3 monoclonal antibody or antigen binding fragment thereof, that comprises a VH of SEQ ID NO: 141 and VL of SEQ ID NO: 140, as described in U.S. Pat. No. 8,735,551;
6) (E)-N-hydroxy-3-(4-(((2-(2-methyl-1H-indol-3-yl) ethyl)amino)methyl)phenyl) acrylamide;
7) (3R)-3-cyclopentyl-3-[4-(7H-pyrrolo-[2,3-d]pyrimidin-4-yl)-1H-pyrazol-1-yl]propanenitrile; and/or
8) 8-(2,6-difluoro-3,5-dimethoxy-phenyl)-quinoxaline-5-carboxylic acid (4-dimethylaminomethyl-1H-imidazol-2-yl)-amide.

In other embodiments, exemplary chemotherapeutic agents include, but are not limited to,
1) 3-(1H-indol-3-yl)-4-[2-(4-methyl-1-piperazinyl)-4-quinazolinyl]-1H-pyrrole-2,5-diane;
2) 5-(2,4-dihydroxy-5-isopropylphenyl)-N-ethyl-4-(4-(morpholinomethyl) phenyl)isoxazole-3-carboxamide;
3) 2-methyl-2-(4-(3-methyl-2-oxo-8-(quinolin-3-yl)-2,3-dihydro-1H-imidazo[4,5-c]quinolin-1-yl)phenyl)propanenitrile (dactolisib);
4) Compound D (CYP17 inhibitor);

5) 4-[3,5-bis(2-hydroxyphenyl)-1H-1,2,4-triazol-1-yl]-benzoic acid (defeasirox);
6) 4,4'-(1H-1,2,4-triazol-1-ylmethylene)bis-benzonitrile (letrozole);
7) (4S,5R)-3-(2'-amino-2-morpholino-4'-(trifluoromethyl)-[4,5'-bipyrimidin]-6-yl)-4-(hydroxymethyl)-5-methyloxazolidin-2-one;
8) (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one;
9) 4-[(4-methyl-1-piperazinyl)methyl]—N-[4-methyl-3-[[4-(3-pyridinyl)-2-pyrimidinyl]amino]phenyl]-methanesulfonate-benzamide;
10) 4-[(R)-6,7-dihydro-5H-pyrrolo[1,2-c]imidazol-5-yl]-3-fluorobenzonitrile (osilodrostat);
11) N-[6-[(2R,6S)-2,6-dimethyl-4-morpholinyl]-3-pyridinyl]-2-methyl-4'(tri fluoromethoxy)-[1,1'-biphenyl]-3-carboxamide, diphosphate (sonidegib phosphate);
12) (R)-2-(5-(4-(6-benzyl-4,5-dimethylpyridazin-3-yl)-2-methylpiperazin-1-yl) pyrazin-2-yl)propan-2-ol;
13) Compound M (human monoclonal antibody to PRLR);
14) 2-(2',3-dimethyl-[2,4'-bipyridin]-5-yl)-N-(5-(pyrazin-2-yl)pyridin-2-yl) acetamide;
15) 7-cyclopentyl-N,N-dimethyl-2-((5-((1R,6S)-9-methyl-4-oxo-3,9-diaza bicyclo[4.2.1]nonan-3-yl)pyridin-2-yl)amino)-7H-pyrrolo[2,3-d]pyrimidine-6-carboxamide;
16) Compound P (FGFR2 and/or FGFR4 antibody drug conjugate, mAb 12425);
17) Compound Q (monoclonal antibody of Fab to M-CSF);
18) N-[(9S,10R,11R,13R)-2,3,10,11,12,13-hexahydro-10-methoxy-9-methyl-1-oxo-9,13-epoxy-1H,9H-diindolo[1,2,3m]pyrrolo[3,4-j][1,7]benzodiazonin-11-yl]—N-methyl-benzamide (midostaurin);
19) 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine;
20) cyclo((4R)-4-(2-aminoethylcarbamoyloxy)-L-prolyl-L-phenylglycyl-D-tryptophyl-L-lysyl-4-0-benzyl-L-tyrosyl-L-phenylalanyl-) (pasireotide diaspartate);
21) 1-amino-5-fluoro-3-[6-(4-methyl-1-piperazinyl)-1H-benzimidazol-2-yl]-2(1H)-quinolinone (dovitinib);
22) 8-(6-methoxy-pyridin-3-yl)-3-methyl-1-(4-piperazin-1-yl-3-trifluoromethyl-phenyl)-1,3-dihydro-imidazo[4,5-c]quinolin-2-one;
23) N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-4,6-diamine;
24) 3-(4-(4-((5-chloro-4-((5-methyl-1H-pyrazol-3-yl)amino)pyrimidin-2-yl)amino)-5-fluoro-2-methylphenyl)piperidin-1-yl)thietane 1, 1-dioxide;
25) 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4- diamine;
26) 5-chloro-N2-(4-(1-ethylpiperidin-4-yl)-2-fluoro-5-methylphenyl)-N4-(5-methyl-1Hpyrazol-3-yl)pyrimidine-2, 4-diamine;
27) 6-[(2S,4R,6E)-4-methyl-2-(methylamino)-3-oxo-6-octenoic acid]cyclo sporine D. Amdray, PSC833, [3'-Desoxy-3'-oxo-MeBmt]1-[Val]2-cyclosporin (valspodar);
28) N-(4-chlorophenyl)-4-(4-pyridinylmethyl)-1-phthalazinamine succinate (vatalanib succinate);
29) Compound CC (IDH inhibitor);
30) (R)-N-(4-(chlorodifluoromethoxy)phenyl)-6-(3-hydroxypyrrolidin-1-yl)-5-(1H-pyrazol-5-yl)nicotinamide;
31) Compound EE (cRAF inhibitor);
32) Compound FF (ERK1/2 ATP competitive inhibitor); and
33) 4-((2-(((1R,2R)-2-hydroxycyclohexyl)amino)benzo[d]thiazol-6-yl)oxy)-N-methylpicolinamide. See, e.g., WO2016/100882, which is incorporated herein by reference in its entirety.

In certain embodiments, exemplary therapeutic agents for conjoint administration are monoclonal antibodies or fragments thereof (see e.g., Bolliger (1993) Proc. Natl. Acad. Sci. USA 90: 6444-6448; Poljak (1994) Structure 2: 1121-1123). These therapeutic monoclonal antibodies and/or fragments thereof include, but are not limited to, anti-LAG-3 monoclonal antibody, anti-PD-1 antibody, anti-PD-L1 antibody, anti-PD-L2 antibody, anti-TIM-3 antibody, anti-CTLA-4 antibody, anti-TIGIT antibody, anti-OX40 antibody, anti-GITR antibody, adalimumab, afatinib, afutuzumab, alemtuzumab, atezolizumab, avelumab, axitinib, basiliximab, bavituximab, belimumab, bevacizumab, brentuximab, canakinumab, certolizumab, cetuximab, daclizumab, denosumab, durvalamab, eculizumab, efalizumab, elotuzumab, fostamatinib, gemtuzumab ozogamicin, golimumab, ibritumomab tiuxetan, infliximab, ipilimumab, lambrolizumab, lapatinib, lenvatinib, lirilumab, mogamulizumab, motavizumab, mubritinib, natalizumab, nivolumab, obinutuzumab, ofatumumab, omalizumab, palivizumab, panitumumab, pegaptani, pembrolizumab, pertuzumab, pidilizumab, ranibizumab, raxibacumab, rilotumumab, rituximab, tocilizumab, tositumomab-I-13, trastuzumab, tremelimumab, urelumab, ustekinumab, and varlilumab.

Combination therapies can also include administration of bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-1 blockade. Alternatively, antigen may be delivered directly to DCs by the use of bispecific antibodies which bind to tumor antigen and a dendritic cell specific cell surface marker.

Other antibodies which may be used to activate host immune responsiveness can be used in combination with the combination therapies described herein. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with PD-1 antibodies (Ito, N. et al. (2000) Immunobiology 201 (5) 527-40). Antibodies to T cell costimulatory molecules such as CTLA-4 (e.g., U.S. Pat. No. 5,811,097), OX-40 (Weinberg. A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Immunomodulatory agents and therapies that are suitable for use in the compositions and conjoint methods described herein include, but are not limited to, anti-T cell receptor antibodies such as anti-CD3 antibodies (e.g., Nuvion (Protein Design Labs), OKT3 (Johnson & Johnson), or anti-CD20 antibodies Rituxan (IDEC)), antiCD52 antibodies (e.g., CAMPATH 1H (Ilex)), anti-CDlla antibodies (e.g., Xanelim (Genentech)); anti-cytokine or anti-cytokine receptor antibodies and antagonists such as anti-IL-2 receptor antibodies (Zenapax (Protein Design Labs)), anti-IL-6 receptor antibodies (e.g., MRA (Chugai)), and anti-IL-12 antibodies (CNT01275 (Janssen)), anti-TNFalpha antibodies (Remicade (Janssen)) or TNF receptor antagonist (Enbrel (Immunex)), anti-IL-6 antibodies (BE8 (Diaclone) and siltuximab (CNT032 (Centocor)), and antibodies that immunospecifically bind to tumor-associated antigens (e.g., trastuzimab (Genentech)).

The combination therapies disclosed herein can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173: 4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

Compounds disclosed herein can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, Net al. (1994) Science 266: 2011-2013). (These somatic tissues may be protected from immune attack by various means). Tumor antigens may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Compounds disclosed herein can be combined with a vaccination protocol. Many experimental strategies for vaccination against tumors have been devised (see Rosenberg, S., 2000, Development of Cancer Vaccines. ASCO Educational Book Spring: 60-62: Logothetis, C., 2000, ASCO Educational Book Spring: 300-302; Khayat. D. 2000, ASCO Educational Book Spring: 414-428; Foon, K. 2000, ASCO Educational Book Spring: 730-738; see also Restifo, N. and Sznol. M., Cancer Vaccines, Ch. 61. pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43). In some embodiments, vaccination with immunoglobulin idiotype produced by malignant plasma cells is used. Other therapeutic vaccines include, but are not limited to, sipuleucel-T, gp100 vaccine. HPV-16 vaccination, and GVAX pancreas vaccine.

Other tumor vaccines may include the proteins from viruses implicated in human cancers such a Human Papilloma Viruses (HPV), Hepatitis Viruses (HBV and HCV). Kaposi's Herpes Sarcoma Virus (KHSV) and Preferentially Expressed Antigen In Melanoma (PRAME). In certain embodiments, the vaccine is selected from a viral vector vaccine, bacterial vaccine, cell-based vaccine, DNA vaccine, RNA vaccine, peptide vaccine, or protein vaccine. See. e.g., Jeffrey Schlom, "Therapeutic Cancer Vaccines: Current Status and Moving Forward," J Natl Cancer Inst; 104: 599-613 (2012). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269: 1585-1588; Tamura, Y. et al. (1997) Science 278:117-120).

Exemplary agents that can be conjointly administered with compounds disclosed herein include a therapeutic cancer vaccine or adoptive T cell therapy. In certain embodiments, the therapeutic cancer vaccine is a dendritic cell vaccine. The dendritic cell vaccine can be composed of autologous dendritic cells and/or allogeneic dendritic cells. In certain embodiments, the autologous or allogeneic dendritic cells are loaded with cancer antigens prior to administration to the subject. In certain embodiments, the autologous or allogeneic dendritic cells are loaded with cancer antigens through direct administration to the tumor. In certain embodiments, the adoptive T cell therapy comprises autologous and/or allogenic T-cells. In certain embodiments, the autologous and/or allogenic T-cells are targeted against tumor antigens.

In certain embodiments, non-limiting examples of cancer vaccines include tumor cell vaccines, antigen vaccines, dendritic cell vaccines, DNA vaccines, and vector based vaccines. Antigen vaccines boost the immune system by using one or more antigens, such as peptides. Antigen vaccines may be specific for a certain type of cancer because each tumor type may be identified by specific antigen profiles. Dendritic cell vaccines are often autologous vaccines, and must often be made individually for each subject. Non-limiting examples of dendritic vaccines are Sipuleucel-T and DCvax. For preparing DNA vaccines, vectors can be engineered to contain specific DNAs that can be injected into a subject which leads to the DNA being taken up by cells. Once the cells take up the DNA, the DNA will program the cells to make specific antigens, which can then provoke the desired immune response.

Pancreatic Cancer

Exemplary agents that that can be used conjointly with compounds disclosed herein for the treatment of pancreatic cancer include, but are not limited to, TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., R05126766); Notch signaling inhibitor (e.g., MK0752); monoclonal antibody-antibody fusion protein (e.g., L19IL2); curcumin; HSP90 inhibitor (e.g., tanespimycin, STA-9090); riL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., R04929097); ribonucleotide reductase inhibitor (e.g., 3-AP); immunotoxin (e.g., HuC242-DM4); PARP inhibitor (e.g., KU-0059436, veliparib); CTLA-4 inhibitor (e.g., CP-675,206, ipilimumab); AdVtk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG 12D LODER; and radiation therapy (e.g., tomotherapy, stereotactic radiation, proton therapy), surgery, and a combination thereof.

Small Cell Lung Cancer

Exemplary agents that that can be used conjointly with compounds disclosed herein to treat small cell lung cancer include, but are not limited to, etoposide, carboplatin, cisplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS833923); peptide cancer vaccine, and radiation therapy (e.g., intensity-modulated radiation therapy (IMRT), hypofractionated radiotherapy, hypoxia-guided radiotherapy), surgery, and combinations thereof.

Non-Small Cell Lung Cancer

Exemplary agents that that can be used conjointly with compounds disclosed herein to treat non-small cell lung cancer include, but are not limited to, vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafurgimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, R05083945), MET inhibitor (e.g., PF-02341066, ARQ 197), PI3K kinase inhibitor (e.g., XL147, GDC-0941), Raf/MEK dual kinase inhibitor (e.g., R05126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25liposome vaccine, GVAX, recombinant DNA and adenovirus expressing L523S protein), Bcl-2 inhibitor (e.g., oblimersen, sodium), proteasome inhibitor (e.g., bortezomib, carfilzomib, NPI-0052, ixazomid), paclitaxel or a paclitaxel agent, docetaxel, IGF-1 receptor inhibitor (e.g., cixutumumab, MK-0646, OSI906, CP-751.871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH$_{589}$, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008). CNGRC peptide-TNF alpha conjugate, dichloroacetate (DCA), HGF inhibitor (e.g., SCH 900105), SAR240550, PPAR-gamma agonist (e.g., CS-7017), gamma-secretase inhibitor (e.g., R04929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OHtransferase inhibitor (e.g., lonafarnib). immunotoxin (e.g., BB-10901, SS1 (dsFv) PE38), fondaparinux, vascular-disrupting agent (e.g., A VE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

Ovarian Cancer

Exemplary agents that that can be used conjointly with compounds disclosed herein to treat ovarian cancer include, but are not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-303), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S 193), statin (e.g., lovastatin), topoisomerase 1 inhibitor (e.g., NKTR -1 02), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., R04929097), Wee-1 inhibitor (e.g., MK-1775), antitubulin agent (e.g., vinorelbine, E7389), immunotoxin (e.g., denileukin diftitox), SB-485232, vascular-disrupting agent (e.g., A VE8062), integrin inhibitor (e.g., EMD 525797), kinesin-spindle inhibitor (e.g., 4SC-205), revlimid, HER2 inhibitor (e.g., MGAH$_{22}$), ErrB3 inhibitor (e.g., MM-121), radiation therapy; and combinations thereof.

Renal Cell Carcinoma

Exemplary agents that that can be conjointly administered with compounds disclosed herein to treat renal cell carcinoma include, but are not limited to, interleukin-2 or interferon-a, a targeted agent (e.g., a VEGF inhibitor such as a monoclonal antibody to VEGF, e.g., bevacizumab (Rini, B. I. et al. (2010) J. Clin. Oncol. 28(13): 2137-2143)); a VEGF tyrosine kinase inhibitor such as sunitinib, sorafenib, axitinib and pazopanib (reviewed in Pal S. K. et al. (2014) Clin. Advances in Hematology & Oncology 12(2): 90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) N. Engl. J. Med. 356(22): 2271-2281, Motzer, R. J. et al. (2008) Lancet 372: 449-456).

Chronic Myelogenous Leukemia

Exemplary agents that that can be conjointly administered with compounds disclosed herein to treat chronic myelogenous leukemia (CML) include, but are not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), a dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., R05045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

Chronic Lymphocyic Leukemia

Exemplary agents that that can be conjointly administered with compounds disclosed herein to treat chronic lymphocyic leukemia (CLL) include, but are not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, R05072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH$_{589}$, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-5016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., R05045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG 186, radiation therapy, bone marrow transplantation, stem cell transplantation, and combinations thereof.

Acute Lymphocyic Leukemia

Exemplary agents that that can be conjointly administered with compounds disclosed herein to treat acute lymphocyic leukemia (ALL) include, but are not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., R05045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, bone marrow transplantation, stem cell transplantation, radiation therapy, and combinations thereof.

Acute Myeloid Leukemia

Exemplary agents that that can be conjointly administered with compounds disclosed herein to treat acute myeloid leukemia (AML) include, but are not limited to, a chemotherapeutic agent (e.g., cytarabine, daunorubicin, idarubicin, clofarabine. decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH$_{589}$), plerixafor, mTOR inhibitor (e.g., everolimus), SRC inhibitor (e.g., dasatinib), HSP90 inhibitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., R05045337), mTOR inhibitor (e.g., everolimus), LY573636-sodium, ZRx-101, MLN4924, lenalidomide, immunotherapy (e.g., AHN-12), histamine dihydrochloride, bone marrow transplantation, stem cell transplantation, radiation therapy, and combinations thereof.

Multiple Myeloma

Exemplary agents that can be conjointly administered with compounds disclosed herein to treat multiple myeloma include, but are not limited to, a chemotherapeutic agent (e.g., melphalan, amifostine, cyclophosphamide, doxorubicin, clofarabine, bendamustine, fludarabine, adriamycin, SyB L-0501), thalidomide, lcnalidomidc, dexamethasone, prednisone, pomalidomide, proteasome inhibitor (e.g., bortezomib, carfilzomib, ixazomid), cancer vaccine (e.g., GVAX), CD-40 targeting agent (e.g., SGN-40, CHIR-12.12), perifosine, zoledronic acid, immunotherapy (e.g., MAGE-A3, NY-ESO-1, HuMax-CD38), HDAC inhibitor (e.g., vorinostat, LBH$_{589}$, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH$_{2101}$, atorvastatin, immunotoxin (e.g., BB- 10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945). bone marrow transplantation, stem cell transplantation, radiation therapy, and combinations thereof.

Prostrate Cancer

Exemplary agents that can be conjointly administered with compounds disclosed herein to treat prostrate cancer include, but are not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab). TRC105, Aurora A kinase inhibitor (e.g., MLN8237), proteasome inhibitor (e.g., bortezomib), OGX-011, radioimmunotherapy (e.g., HuJ591-GS). HDAC inhibitor (e.g., valproic acid, SB939, LBH$_{589}$), hydroxychloroquine, mTOR inhibitor (e.g., everolimus), dovitinib lactate, diindolylmethane, efavirenz, OGX-427, genistein, IMC-303, bafetinib, CP-675,206, radiation therapy, surgery, or a combination thereof.

Hodgkin's Lymphomas

Exemplary agents that that can be used conjointly with compounds disclosed herein for the treatment of Hodgkin's lymphomas include, but are not limited to, chemotherapeutics such as Doxorubicin (Adriamycin), bleomycin (Blenoxane), vinblastine (Velban, Velsar), dacarbazine, etoposide (Toposar, VePcsid), cyclophosphamide (Cytoxan, Neosar), vincristine (Vincasar PFS, Oncovin), procarbazine (Matulane), prednisone, Ifosfamide (Ifex), carboplatin (Paraplatin), Mechlorethamine, Chlorambucil, methylprenisolone (Solu-Medrol), cytarabine (Cytosar-U), cisplatin (Platinol), Gemcitabine (Gemzar), vinorelbine (Navelbine), oxaliplatin (Eloxatin), Lomustine, Mitoxantrone, carmustine, melphalan, Bendamustine, Lenalidomide, and vinorelbine; either alone or in combinations; Brentuximab vedotin (Adcetris—a CD30 anti-body drug conjugate); Iodine131—CHT25 antibody conjugate; HDAC inhibitors (e.g., vorinostat); m-TOR inhibitors (e.g., everolimus, temsirolimus); PI3K inhibitors (e.g., CAL-101, BAY80-6946, TGR-1202, BKM-120, AMG-319); JAK/STAT pathway inhibitors; Bcl-2 inhibitors (e.g., venetoclax); Mcl-1 inhibitors; multikinase inhibitors such as BAY 43-9006 (sorafenib); proteasome inhibitors (e.g., bortezomib (Velcade), NPI-0052); dual PI3K/HDAC targeted inhibitors (e.g., CUDC-907); NF-KB inhibitors; anti-PD-1 antibodies (e.g., nivolumab, pembrolizumab); anti-CTLA-4 antibodies (e.g., ipilimumab); anti-CD-20 antibodies (e.g., rituximab); anti-CD40 antibodies; anti-CD80 antibodies; and radiation therapy (e.g., tomotherapy, stereotactic radiation, proton therapy), surgery, and a combination thereof.

Non-Hodgkin's Lymphomas

Exemplary agents that that can be used conjointly with compounds disclosed herein for the treatment of Hodgkin's lymphomas include, but are not limited to, chemotherapeutics such as Doxorubicin (Adriamycin), bleomycin (Blenoxane), dacarbazine, etoposide (Toposar, VePesid), vinblastine (Velban. Velsar), cyclophosphamide (Cytoxan, Neosar), vincristine (Vincasar PFS, Oncovin), procarbazine (Matulane), prednisone. Ifosfamide (Ifex), carboplatin (Paraplatin), Mechlorethamine, Chlorambucil, methylprenisolone (Solu-Medrol), cytarabine (Cytosar-U), cisplatin (Platinol). Gemcitabine (Gemzar), vinorelbine (Navelbine), oxaliplatin (Eloxatin), Lomustine, Mitoxantrone, methotrexate, carmustine, melphalan, Bendamustine, Lenalidomide, and vinorelbine; either alone or in combinations; tyrosine kinase inhibitors (e.g., EGFR inhibitor (e.g., erlotinib, panitumumab, cetuximab, nimotuzumab); HDAC inhibitors (e.g., vorinostat); IRAK-4 inhibitors; HSP90 inhibitors (e.g., tanespimycin, STA-9090, CUDC-305); m-TOR inhibitors (e.g., everolimus, temsirolimus); PI3K inhibitors (e.g., CAL-101, BAY80-6946, TGR-1202, BKM-120, AMG-319); JAK/STAT pathway inhibitors; AKT inhibitors (e.g., RX-0201); Bcl-2 inhibitors (e.g., venetoclax); Mcl-1 inhibitors; multikinase inhibitors such as BAY 43-9006 (sorafenib); proteasome inhibitors (e.g., bortezomib (Velcade), NPI-0052); dual PI3K/HDAC targeted inhibitors (e.g., CUDC-907); NF-KB inhibitors; BTK inhibitors (e.g., ibrutinib); BET bromodomain inhibitors; anti-PD-1 antibodies (e.g., nivolumab. pembrolizumab); anti-CTLA-4 antibodies (e.g., ipilimumab); anti-CD20 antibodies (e.g., rituximab); anti-CD30 antibodies (e.g., brentuximab vedotin); anti-CD40 antibodies; anti-CD80 antibodies; and radiation therapy (e.g., tomotherapy, stereotactic radiation, proton therapy), surgery, and a combination thereof.

In certain embodiments, a compound of Formula (I) of the disclosure may be conjointly administered with non-chemical methods of cancer treatment. In a further embodiment, a compound of Formula (I) of the disclosure may be conjointly administered with radiation therapy. In a further embodiment, a compound of Formula (I) of the disclosure may be conjointly administered with surgery, with thermoablation, with focused ultrasound therapy, with cryotherapy, or with any combination of these.

In certain embodiments, different compounds of the disclosure may be conjointly administered with one or more other compounds of the disclosure. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound of Formula (I) of the disclosure provides a synergistic effect. In certain embodiments, conjointly administering one or more additional chemotherapeutics agents provides an additive effect.

Pharmaceutical Compositions

In certain embodiments, the present disclosure provides a pharmaceutical composition comprising a compound of Formula (I) as disclosed herein, optionally admixed with a pharmaceutically acceptable carrier or diluent.

The present disclosure also provides methods for formulating the disclosed compounds of Formula (I) for pharmaceutical administration.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of Formula (I) of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of Formula (I) of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of Formula (I) of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient. preferably from about 5 percent to about 70 percent, most preferably from about 10 percent to about 30 percent.

Methods of preparing these formulations or compositions include the step of bringing into association an active compound, such as a compound of Formula (I) of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostcarate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries. tampons, creams, gels, pastes, foams or spray formulations containing such carriers as are known in the art to be appropriate.

Dosage forms for the topical or transdermal administration include powders. sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference in its entirety. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

A suppository also is contemplated as being within the scope of this disclosure.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions. or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of Formula (I) of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless defined otherwise, all technical and scientific terms used herein have the same meaning as is commonly understood by one of skill in art to which the subject matter herein belongs. As used herein, the following definitions are supplied in order to facilitate the understanding of the present disclosure.

The term "acyl" is art-recognized and refers to a group represented by the general formula hydrocarbylC(O)—, preferably alkylC(O)—. Acyl groups include —C(O)CH$_3$, —C(O)CH$_2$CH$_3$ and the like.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A C$_1$-C$_6$ straight chained or branched alkyl group is also referred to as a "lower alkyl" group. An alkyl group may be optionally substituted at one or more positions as permitted by valence. Such optional substituents include, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds. A cycloalkyl group may be substituted at one or more positions, as permitted by valence, with any optional substituents described herein. Cycloalkyl groups include but are not limited to cyclopropyl, cyclobutyl, cyclopentyl and cyclohexyl.

The term "carboxy" or "carboxylic acid", as used herein, refers to a group represented by the formula —CO$_2$H. The term "carboxylate" refers to a group represented by the formula —(CO$_2$)$^-$.

The term "guanidino", as used herein, refers to —NH—C(=NH)—NH$_2$ group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, indole, 1,2,4-oxadiazole, 1,2,4-thiadiazole, 1,3,4-oxadiazole, 1,3,4-thiadiazole, benzimidazole, pyrimidine, and the like. A heteroaryl group may be substituted at one or more positions, as permitted by valence, with any optional substituents described herein.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom. preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine. morpholine, azepane, azetidine, 2,3-dihydrobenzo[b][1,4]dioxine, tetrahydro-2H-pyran. lactones, lactams, and the like. Heterocyclyl groups may be optionally substituted as permitted by valence.

As used herein, the term "hydroxy" or "hydroxyl" refers to —OH group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine. an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present disclosure (e.g., a compound of formula (I)). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present disclosure. In certain embodiments, some or all of the compounds of formula (I) in a formulation represented above can be replaced with the corresponding suitable prodrug, e.g., wherein a hydroxyl in the parent compound is presented as an ester or a carbonate or carboxylic acid present in the parent compound is presented as an ester.

As used herein, the term "comprise" or "comprising" is generally used in the sense of include, that is to say permitting the presence of one or more additional (unspecified) features or components.

As used herein, the term "including" as well as other forms, such as "include", "includes," and "included," is not limiting.

As used herein, the term "amino acid" means a molecule containing both an amino group and a carboxyl group, and includes its salts, esters, combinations of its various salts, as well as tautomeric forms. In solution, at neutral pH, amino and acid groups of an amino acid can exchange a proton to form a doubly ionized, through overall neutral, entity identified as a zwitterion. In some embodiments, the amino acids are $\alpha$-, $\beta$-, $\gamma$-, or $\delta$-amino acids, including their stereoisomers and racemates. As used herein, the term "L-amino acid" denotes an $\alpha$-amino acid having the levorotatory configuration around the $\alpha$-carbon, that is, a carboxylic acid of general formula $CH(COOH)(NH_2)$-(side chain), having the L-configuration. The term "D-amino acid" similarly denotes a carboxylic acid of general formula $CH(COOH)(NH_2)$-(side chain), having the dextrorotatory-configuration around the a-carbon. Side chains of L-amino acids can include naturally occurring and non-naturally occurring moieties. Non-naturally occurring (i.e., unnatural) amino acid side chains are moieties that are used in place of naturally occurring amino acid side chains in, for example, amino acid analogs.

An "amino acid residue" as used herein, means a moiety sharing structural similarity to the parent amino acid. An amino acid residue may be covalently bonded to another chemical moiety via the amino group of the residue, or the carboxylate group of the residue (i.e., a hydrogen atom of —$NH_2$ or —OH is replaced by a bond to another chemical moiety).

Amino acids include the twenty standard amino acids used by most biological organisms in protein synthesis. Unnatural amino acid residues may be selected from, but are not limited to, alpha and alpha-disubstituted amino acids, N-alkyl amino acids, and natural amino acids substituted with lower alkyl, aralkyl, hydroxyl, aryl, aryloxy, heteroarylalkyl or acyl.

For example, lysine can be substituted to form an unnatural amino acid, e.g., at a carbon atom of its side chain, or alternatively by mono- or dialkylation of its terminal $NH_2$ group (e.g., wherein the amino group of the lysine sidechain is taken together with its substituents to form a heterocyclic ring such as piperidine or pyrrolidine). In another example, the terminal amino group of the lysine sidechain can form a ring with the amino acid backbone, as in capreomycidine. Further unnatural derivatives of lysine include homolysine and norlysine. The sidechain of lysine can alternatively be substituted with a second amino group. In another example, the alkyl portion of the lysine side chain can be incorporated into a carbocyclic ring structure to form a semirigid analog, such as, e.g., cyclohexyl or cyclopentyl.

Throughout this specification and claims, the 'L-threonine residue' and/or 'side chain of L-threonine' mentioned in compound of formula (I) thereof can be represented by any one of the following formulae:

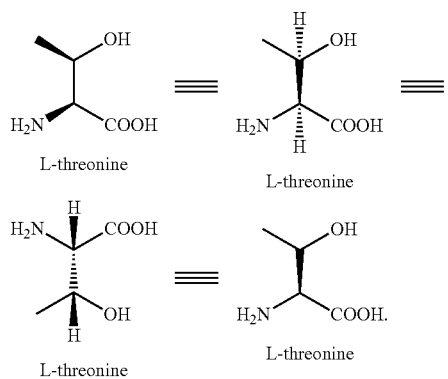

In certain embodiments, the unnatural amino acid can be a derivative of a natural amino acid having one or more double bonds.

In other example embodiments, in threonine, the beta-methyl group can be replaced with an ethyl, phenyl, or other higher alkyl group. In histidine, the imidazole moiety can be substituted, or alternatively, the alkylene backbone of the side chain can be substituted.

Further examples of unnatural amino acids include homoserine, and homologs of natural amino acids.

In further example embodiments, an unnatural amino acid can be alkylated (e.g., methylated) at the alpha position.

Further examples of unnatural amino acids include alpha, beta- and beta,gamma-dehydroamino amino acid analogs.

Further exemplary amino acids include penicillamine and betamethoxyvaline.

Further examples of unnatural amino acids include the amino acids wherein the side chain comprises amino, alkylamino, acylamino, —COO-alkyl, cycloalkyl, heterocyclyl, heteroaryl, guanidino, (cycloalkyl)alkyl, (heterocyclyl)alkyl and (heteroaryl)alkyl.

"Modified N-terminal amino group" and "modified C-terminal carboxyl group" mean that the amino group or carboxyl group is altered.

Modification of the N-terminal amino group is preferably with the general formula —$NR_xR_y$; wherein $R_x$ is hydrogen or alkyl and $R_y$ is alkyl, alkenyl, —C(=NH)$NH_2$, alkynyl or acyl.

Examples of N-terminal modifications include, but are not limited to, are acetylated, formylated or guanylated N-termini.

Modification of the C-terminal carboxyl group is preferably with the general formula $COR_z$ ($R_z$ replaces the hydroxyl group of the last amino acid); wherein $R_z$ is —$NR_bR_c$, alkoxy, amino or an imide. For example, the C-terminus may be esterified or amidated.

This disclosure includes pharmaceutically acceptable salts of compounds of the disclosure and their use in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "stereoisomers" refers to any enantiomers, diastereoisomers, or geometrical isomers, such as of the compounds of the disclosure. When compounds of the disclosure are chiral, they can exist in racemic or in optically active form. Since the pharmaceutical activity of the racemates or stereoisomers of the compounds according to the disclosure may differ, it may be desirable to use compounds that are enriched in one of the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

In certain embodiments, compounds of the disclosure may be racemic. In certain embodiments, compounds of the disclosure may be enriched in one enantiomer. For example, a compound of Formula (I) of the disclosure may have greater than 30% ee, 40% ee, 50% ee, 60% ee, 70% ee, 80% ee, 90% ee, or even 95% or greater ee. In certain embodiments, compounds of the disclosure may have more than one stereocenter. In certain such embodiments, compounds of the disclosure may be enriched in one or more diastereomer. For example, a compound of Formula (I) of the disclosure may have greater than 30% de, 40% de, 50% de, 60% de, 70% de, 80% de, 90% de, or even 95% or greater de.

The term "subject" includes mammals (especially humans) and other animals, such as domestic animals (e.g., household pets including cats and dogs) and non-domestic animals (such as wildlife).

Naturally-occurring amino acids (L-form) are identified throughout the description and claims by the conventional three-letter abbreviations indicated in the below table.

TABLE 6

(Amino acid codes)

| Name | 3-letter code |
|---|---|
| Alanine | Ala |
| Arginine | Arg |
| Asparagine | Asn |
| Aspartic acid | Asp |
| Glutamic acid | Glu |
| Glutamine | Gln |
| Isoleucine | Ile |
| Lysine | Lys |
| Methionine | Met |
| Phenylalanine | Phe |
| Proline | Pro |
| Serine | Ser |
| Threonine | Thr |
| Tyrosine | Tyr |
| Valine | Val |

The abbreviations used in the entire specification may be summarized herein below with their particular meaning.

° C. (degree Celsius); % (percentage); g or gm (gram); h or hr (Hours); mM (Millimolar); M (Molar); μM (Micromolar); mL (Millilitre); μL or μl (Microlitre); um (Micrometer); min (Minutes); nm (Nanometer); PD-1/PD1 (Programmed cell death 1); PD-L1 (Programmed death-ligand 1); PD-L2 (Programmed cell death 1 ligand 2); T-cell immunoglobulin and mucin-domain containing-3 (TIM-3); etc.

The synthetic procedures for the preparation of compounds of the present invention were described in WO2016142833 A1, WO2016142886 A2 and WO2015033299 A1.

EXAMPLES

Example 1: Rescue of Mouse Splenocyte Proliferation in the Presence of Recombinant PD-L1/PD-L2

Recombinant mouse PD-L1 (rm-PDL-1, cat no: 1019-B7-100; R&D Systems) were used as the source of PD-L1.
Requirements Mouse splenocytes harvested from 6-8 weeks old C57 BL6 mice; RPMI 1640 (GIBCO, Cat #11875); DMEM with high glucose (GIBCO, Cat #D6429); Fetal Bovine Serum [Hyclone, Cat #SH30071.03]; Penicillin (10000 unit/mL)-Streptomycin(10,000 μg/mL) Liquid (GIBCO, Cat #15140-122); MEM Sodium Pyruvate solution 100 mM (100×), Liquid (GIBCO. Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO. Cat #-A10492); Histopaque (density-1.083 gm/mL) (SIGMA 10831); Trypan blue solution (SIGMA-T8154); 2 mL Norm Ject Luer Lock syringe-(Sigma 2014-12); 40 μm nylon cell strainer (BD FALCON 35230); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 μL of Dimethyl sulfoxide (DMSO $C_2H_6SO$, SIGMA-D-5879) and aliquoted in to tubes for further use. Working concentrations were titrated from 10 μM to 1 μM. (eBioscience-650850-85); 0.05% Trypsin and 0.02% EDTA (SIGMA 59417C); 96-well format ELISA plates (Corning CLS3390); BD FACS caliber (E6016); Recombinant mouse B7-H1/PDL1 Fc Chimera, (rm-PD-L1 cat no: 1019-B7-100).
Protocol
Splenocyte Preparation and Culturing Splenocytes harvested in a 50 mL falcon tube by mashing mouse spleen in a 40 um cell strainer were further treated with 1 mL ACK lysis buffer for 5 min at room temperature. After washing with 9 mL of RPMI complete media, cells were re-suspended in 3 mL of 1× PBS in a 15 mL tube. 3 mL of Histopaque was added carefully to the bottom of the tube without disturbing overlaying splenocyte suspension. After centrifuging at 800× g for 20 min at room temperature, the opaque layer of splenocytes was collected carefully without disturbing/mixing the layers. Splenocytes were washed twice with cold 1× PBS followed by total cell counting using Trypan Blue exclusion method and used further for cell based assays.

Splenocytes were cultured in RPMI complete media (RPMI+10% fetal bovine serum+1 mM sodium pyruvate+ 10,000units/mL penicillin and 10,000 μg/mL streptomycin) and maintained in a $CO_2$ incubator with 5% $CO_2$ at 37° ° C.
CFSE Proliferation Assay CFSE is a dye that passively diffuses into cells and binds to intracellular proteins, $1 \times 10^6$ cells/mL of harvested splenocytes were treated with 5 μM of CFSE in pre-warmed 1×PBS/0.1% BSA solution for 10 min at 37° C. Excess CFSE was quenched using 5 volumes of ice-cold culture media to the cells and incubated on ice for 5 min. CFSE labelled splenocytes were further given three washes with ice cold complete RPMI media. CFSE labelled $1 \times 10^5$ splenocytes added to wells containing either MDA-MB231 cells ($1 \times 10^5$ cells cultured in high glucose DMEM medium) or recombinant human PDL-1 (100 ng/mL) and test compounds. Splenocytes were stimulated with anti-mouse CD3 and anti- mouse CD28 antibody (1 μg/mL each), and the culture was further incubated for 72 h at 37° C. with 5% $CO_2$. Cells were harvested and washed thrice with ice cold FACS buffer and % proliferation was analysed by flow cytometry with 488 nm excitation and 521 nm emission filters.
Data Compilation, Processing and Inference Percent splenocyte proliferation was analysed using cell quest FACS program and percent rescue of splenocyte proliferation by compound was estimated after deduction of % background proliferation value and normalising to % stimulated splenocyte proliferation (positive control) as 100%.

Stimulated splenocytes: Splenocytes+anti-CD3/CD28 stimulation

Background proliferation: Splenocytes+anti-CD3/CD28+ PD-L1

Compound proliferation: Splenocytes+anti-CD3/CD28+ PD-L1+Compound

Compound effect is examined by adding required conc. of compound to anti-CD3/CD28 stimulated splenocytes in presence of ligand (PDL-1).

Example 2: Rescue of Mouse Splenocyte Proliferation in the Presence of Recombinant TIM-3

Requirements

Vehicle: Milli Q water; RPMI 1640 (GIBCO, Cat #11875); Fetal Bovine Serum [Hyclone, Cat #SH30071.03]; Penicilin (10000 unit/ml)-Streptomycin(10,000 μg/ml) liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Recombinant human TIM-3 (rhGi24 TIM-3/B7-$H_5$ Fc chimera (R&D systems, cat no: 7126-B7); Anti-h/m Gi24/TIM-3/B7-$H_5$ purified mouse monoclonal IgG2B (R&D systems, cat no: MAB7126); Mouse IgG2B isotype control (R&D Systems cat no: MAB 004); Anti human-CD3 antibody (eBiosciences—16-0039); Anti human-CD28 antibody (eBiosciences—16-0289); Histopaque (density-1.077 gm/ml) (SIGMA 1077); Trypan Blue solution (SIGMA-T8154); Hemacytometer (Bright line-SIGMA Z359629); FACS Buffer containing Phosphate Buffered Saline (PBS) pH 7.2; (HiMedia TS1006) with 0.1% Bovine Serum Albumin (BSA) (SIGMA A7050) and sodium azide (SIGMA 08591); 96-well format ELISA plates (Corning 3599); 96-well format ELISA plates (Corning 3361); BD FACS caliber (E6016); Centrifuge (Eppendorf 5810 R); Human IFN-γ Duo set ELISA kit (R&D Systems; cat no: DY-285).

Protocol

Human PBMC IFN-γ Release Assay 96-well cell culture plates were pre-coated with recombinant human TIM-3 (2.5 μg/ml) and anti-human CD3 (2.5 μg/ml), and stored at 4° C. overnight. Anti-human TIM-3 and isotype control antibodies were either coated along with the TIM-3 or incubated for 30 min next day before addition of cells. On the next day, plates were washed with 1× PBS and then incubated with test compounds for 30 min. Isolated PBMC (0.1×10$^6$ cells/well) and anti-human CD28 antibodies (1 μg/ml) were added to the wells. The culture was further incubated for 72 h at 37° C. with 5% $CO_2$. After 72 h of incubation the cell culture supernatants were collected after brief centrifugation at 200 g× 5 min at 4° C. and processed for human IFN-γ measurement by ELISA following manufacturer's protocol (R&D Systems; DY-285).

In brief, 96-well ELISA plates were coated with 100 μl/well of capture antibody in coating buffer and incubated overnight at 4° C. Plates were washed five times with wash buffer and further blocked with 200 μl of 1× assay diluents for 1 hr at RT. Following wash step, 100 μl of cell culture supernatants were added to wells and further incubated for 2 hr at RT. Appropriate standards were also included. After wash step, plate was incubated for one hour with 100 μl/well of detection antibody. The wash step was repeated and the plate was incubated for 30 min with 100 μl/well of Avidin-HRP.

The plate was washed four times with wash buffer and subsequently incubated for 15 min with 100 μl/well of substrate solution, 50 μl of stop solution was added to each well and the plate was read at 450 nm using Gen5 ver 2.05. Delta OD values were used for calculating the concentrations. The absorbance values were plotted against the standards and the concentration of IFN-γ was determined using GraphPad Prism software. Each experimental condition was carried out in triplicates.

Exemplary compounds of the present invention were screened in the above mentioned assay and the results are summarized in Table 7. The percent rescue of IFN-γ release of the selected compounds of present invention are set forth below wherein "A" refers to compounds having more than 70% rescue of IFN-γ release, "B" refers to compounds having rescue of IFN-γ release ranges from 50% to 69.9% and "C" refers to compounds having less than 50% rescue of IFN-γ release.

TABLE 7

| Compound No. | PDL1 (rescue of proliferation @100 nM) | TIM-3 (rescue of IFN γ release @100 nM) |
| --- | --- | --- |
| 1 | 68 | B |
| 2 | 73 | A |
| 3 | 62 | A |
| 4 | 52 | C |
| 5 | 88 | A |
| 6 | 52 | A |
| 7 | 74 | A |
| 8 | 68 | B |
| 9 | 138 | C |
| 10 | 53 | C |
| 11 | 60 | C |
| 12 | 41 | A |
| 13 | 66 | C |
| 14 | 84 | C |
| 15 | 50 | C |
| 16 | 92 | B |
| 17 | 57 | C |
| 18 | 57 | C |
| 19 | 54 | C |
| 20 | 37 | C |
| 21 | 50 | C |
| 22 | 90 | C |
| 23 | 47 | C |
| 24 | 65 | A |
| 25 | 70 | A |
| 26 | 53 | B |

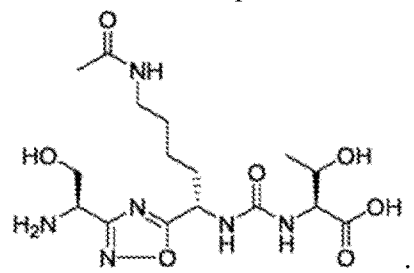

We claim:

1. A method of modulating an immune response mediated by T-cell immunoglobulin and mucin-domain containing-3 (TIM-3) activity in a subject, comprising administering to the subject a compound, wherein the compound is

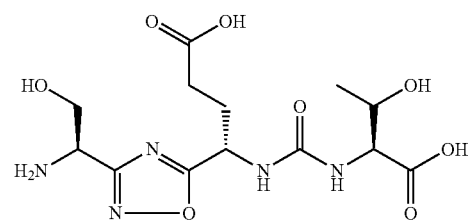 [SMILES: CC(O)[C@H](NC(=O)N[C@@H](CCC(=O)O)c1nc([C@@H](N)CO)no1)C(=O)O]

or a pharmaceutically acceptable salt thereof.

2. The method of claim 1, wherein the compound is

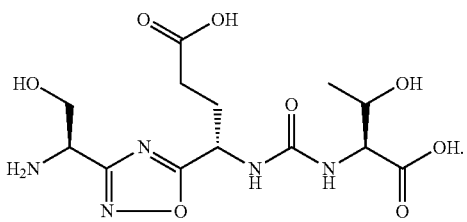 [SMILES: CC(O)[C@H](NC(=O)N[C@@H](CCC(=O)O)c1nc([C@@H](N)CO)no1)C(=O)O]

3. The method of claim 1, wherein the compound is a pharmaceutically acceptable salt of

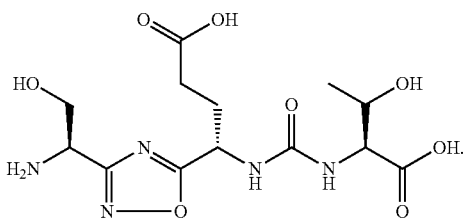 [SMILES: CC(O)[C@H](NC(=O)N[C@@H](CCC(=O)O)c1nc([C@@H](N)CO)no1)C(=O)O]

4. The method of claim 1, wherein the immune response is further mediated by the programmed cell death 1 (PD-1) signaling pathway.

5. The method of claim 2, wherein the immune response is further mediated by the programmed cell death 1 (PD-1) signaling pathway.

6. The method of claim 3, wherein the immune response is further mediated by the programmed cell death 1 (PD-1) signaling pathway.

7. The method of claim 1, wherein the subject is suffering from a disease or disorder selected from cancer, an immune disorder, an immunodeficiency disorder, an inflammatory disorder, an infectious disease, and transplant rejection; and the method treats the disease or disorder.

8. The method of claim 7, wherein the disease or disorder is cancer.

9. The method of claim 8, wherein the cancer is selected from breast cancer, colon cancer, liver cancer, ovarian cancer, prostate cancer, renal cancer, and uterine cancer.

10. The method of claim 8, wherein the cancer is a hematopoietic cancer.

11. The method of claim 10, wherein the hematopoietic cancer is selected from lymphoma, B cell lymphoma, T cell lymphoma, Burkitt's lymphoma, Hodgkin's lymphoma, non-Hodgkin's lymphoma, a leukemia, a myeloma, acute myelogenous leukemia (AML), acute lymphoblastic leukemia (ALL), chronic myelogenous leukemia (CML), chronic lymphoblastic leukemia (CLL), chronic myelomonocytic leukemia (CMML), multiple myeloma, myelodysplastic syndrome (MDS), and plasmacytoma.

12. The method of claim 8, wherein the cancer is selected from ovarian cancer, colon cancer, breast cancer, lung cancer, a myeloma, a neuroblastic-derived CNS tumor, a monocytic leukemia, a B-cell derived leukemia, a T-cell derived leukemia, a B-cell derived lymphoma, a T-cell derived lymphoma, and a mast cell derived tumor.

13. The method of claim 8, wherein the cancer is selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, connective tissue cancer, eye cancer, throat cancer, oral cavity cancer, biliary tract cancer, stomach cancer, testicular cancer, carcinoma of the fallopian tubes, endometrial cancer, cervical cancer, vaginal cancer, vulval cancer, cancer of the esophagus, cancer of the small intestine, cancer of the endocrine system, thyroid cancer, cancer of the parathyroid gland, cancer of the adrenal gland, sarcoma, cancer of the urethra, cancer of the penis, chronic or acute leukemia, acute lymphocytic leukemia (ALL), acute myeloid leukemia (AML), chronic lymphocytic leukemia (CLL), chronic myelogenous leukemia (CML), myeloproliferative disorder/neoplasm (MPDS), myelodysplasia syndrome, a monocytic leukemia, a B-cell derived leukemia, a T-cell derived leukemia, solid tumors of childhood, a B-cell derived lymphoma, T-cell derived lymphoma, Hodgkin's lymphoma, indolent and aggressive non-Hodgkin's lymphoma, Burkitt's lymphoma, follicular lymphoma, mesothelioma, thymic carcinoma, myeloma, multiple myeloma, giant cell myeloma, heavy-chain myeloma, light chain or Bence-Jones myeloma, a mast cell derived tumor, leiomyoma, leiomyosarcoma, glioma, cancer of the bladder, cancer of the ureter, carcinoma of the renal pelvis, liver cancer, pancreatic cancer, post-transplant lymphoproliferative disorder (PTLD), neuroblastic-derived CNS tumors, neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, Meigs' syndrome, Merkel cell carcinoma, and environmentally induced cancers.

14. The method of claim 7, wherein the disease or disorder is an immune disorder, immunodeficiency disorder, or an inflammatory disease.

* * * * *

UNITED STATES PATENT AND TRADEMARK OFFICE
CERTIFICATE OF CORRECTION

| | |
|---|---|
| PATENT NO. | : 12,226,402 B2 |
| APPLICATION NO. | : 18/516458 |
| DATED | : February 18, 2025 |
| INVENTOR(S) | : Pottayil Govindan N. Sasikumar et al. |

It is certified that error appears in the above-identified patent and that said Letters Patent is hereby corrected as shown below:

In the Specification

In Column 13, compound 1, the formula should appear as follows:

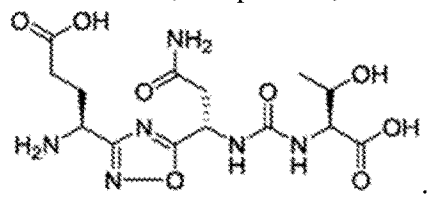

In Column 19, compound 20, the formula should appear as follows:

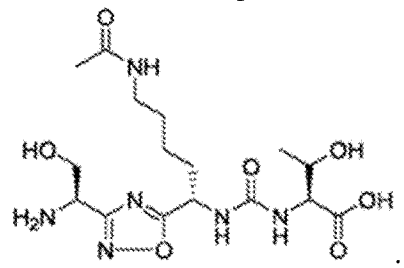

In Column 19, compound 24, the formula should appear as follows:

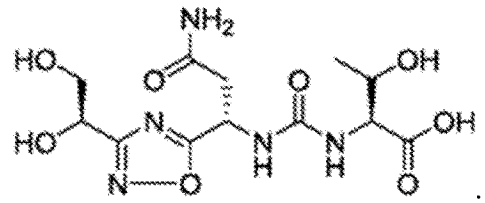

Signed and Sealed this
Eighth Day of April, 2025

Coke Morgan Stewart
*Acting Director of the United States Patent and Trademark Office*

CERTIFICATE OF CORRECTION (continued)
U.S. Pat. No. 12,226,402 B2

In Column 27, compound 20, the formula should appear as follows: